(12) United States Patent
Jackson (10) Patent No.: US 8,911,477 B2
(45) Date of Patent: Dec. 16, 2014

(54) DYNAMIC STABILIZATION MEMBER WITH END PLATE SUPPORT AND CABLE CORE EXTENSION

(76) Inventor: Roger P. Jackson, Prairie Village, KS (US)

( * ) Notice: Subject to any disclaimer, the term of this patent is extended or adjusted under 35 U.S.C. 154(b) by 1341 days.

(21) Appl. No.: 12/288,454

(22) Filed: Oct. 21, 2008

(65) Prior Publication Data

US 2009/0105820 A1  Apr. 23, 2009

Related U.S. Application Data

(60) Provisional application No. 61/000,955, filed on Oct. 30, 2007, provisional application No. 60/999,965, filed on Oct. 23, 2007.

(51) Int. Cl.
*A61B 17/70* (2006.01)

(52) U.S. Cl.
CPC ........... *A61B 17/7004* (2013.01); *A61B 17/702* (2013.01); *A61B 17/7037* (2013.01)
USPC ............................ 606/254; 606/257; 606/259

(58) Field of Classification Search
CPC ............. A61B 17/7004; A61B 17/702; A61B 17/7019; A61B 17/7023; A61B 17/7026; A61B 17/7022; A61B 17/7025; A61B 17/7031
USPC .................................................. 606/254–261
See application file for complete search history.

(56) References Cited

U.S. PATENT DOCUMENTS

| | | |
|---|---|---|
| 2,243,717 A | 5/1941 | Moreira |
| 3,236,275 A | 2/1966 | Smith |
| 3,604,487 A | 9/1971 | Gilbert |
| 3,640,416 A | 2/1972 | Temple |
| 4,041,939 A | 8/1977 | Hall |
| 4,373,754 A | 2/1983 | Bollfrass et al. |
| 4,448,191 A | 5/1984 | Rodnyansky et al. |
| 4,484,570 A | 11/1984 | Sutter et al. |
| 4,600,224 A | 7/1986 | Blose |
| 4,653,486 A | 3/1987 | Coker |
| 4,703,954 A | 11/1987 | Ortloff et al. |
| 4,707,001 A | 11/1987 | Johnson |

(Continued)

FOREIGN PATENT DOCUMENTS

| | | |
|---|---|---|
| DE | G9202745.8 | 4/1992 |
| DE | 4239716 | 8/1994 |

(Continued)

OTHER PUBLICATIONS

*EBI Omega* 21 Brochure, EBI Spine Systems, pub. 1999.

(Continued)

*Primary Examiner* — Eduardo C Robert
*Assistant Examiner* — Julianna N Harvey
(74) *Attorney, Agent, or Firm* — John C. McMahon (57) ABSTRACT

A dynamic fixation medical implant having at least two bone anchors includes a dynamic longitudinal connecting member assembly having the following features: a pair of elongate segments, each segment having at least one and up to a plurality of integral fins axially extending therefrom; an inner cable fixed to one of the elongate segments and slidingly received in the other elongate segment; a molded spacer that substantially surrounds the fins and may partially or substantially surround the abutment plates; a bumper; a crimp ring; and optional sleeves having abutment plates and fins for placement between elongate segments.

32 Claims, 4 Drawing Sheets

(56) References Cited

U.S. PATENT DOCUMENTS

| | | |
|---|---|---|
| 4,743,260 A | 5/1988 | Burton |
| 4,748,260 A | 5/1988 | Marlett |
| 4,836,196 A | 6/1989 | Park et al. |
| 4,887,596 A | 12/1989 | Sherman |
| 4,946,458 A | 8/1990 | Harms et al. |
| 4,950,269 A | 8/1990 | Gaines, Jr. |
| 5,005,562 A | 4/1991 | Cotrel |
| 5,022,791 A | 6/1991 | Isler |
| 5,034,011 A | 7/1991 | Howland |
| 5,042,982 A | 8/1991 | Harms et al. |
| 5,067,955 A | 11/1991 | Cotrel |
| 5,092,635 A | 3/1992 | DeLange et al. |
| 5,102,412 A | 4/1992 | Rogozinski |
| 5,129,388 A | 7/1992 | Vignaud et al. |
| 5,147,363 A | 9/1992 | Harle |
| 5,154,719 A | 10/1992 | Cotrel |
| 5,176,483 A | 1/1993 | Baumann et al. |
| 5,176,678 A | 1/1993 | Tsou |
| 5,176,679 A | 1/1993 | Lin |
| 5,176,680 A | 1/1993 | Vignaud et al. |
| 5,180,393 A | 1/1993 | Commarmond |
| 5,207,678 A | 5/1993 | Harms et al. |
| 5,217,497 A | 6/1993 | Mehdian |
| 5,257,993 A | 11/1993 | Asher et al. |
| 5,261,907 A | 11/1993 | Vignaud et al. |
| 5,261,912 A | 11/1993 | Frigg |
| 5,275,601 A | 1/1994 | Gogolewski et al. |
| 5,282,863 A | 2/1994 | Burton |
| 5,306,275 A | 4/1994 | Bryan |
| 5,312,404 A | 5/1994 | Asher et al. |
| 5,321,901 A | 6/1994 | Kelly |
| 5,346,493 A | 9/1994 | Stahurski et al. |
| 5,358,289 A | 10/1994 | Banker et al. |
| 5,360,431 A | 11/1994 | Puno et al. |
| 5,375,823 A | 12/1994 | Navas |
| 5,385,583 A | 1/1995 | Cotrel |
| 5,395,371 A | 3/1995 | Miller et al. |
| 5,409,488 A | 4/1995 | Ulrich |
| 5,415,661 A | 5/1995 | Holmes |
| 5,423,816 A | 6/1995 | Lin |
| 5,427,418 A | 6/1995 | Watts |
| 5,429,639 A | 7/1995 | Judet |
| 5,443,467 A | 8/1995 | Biedermann et al. |
| 5,466,237 A | 11/1995 | Byrd, III et al. |
| 5,466,238 A | 11/1995 | Lin |
| 5,468,241 A | 11/1995 | Metz-Stavenhagen et al. |
| 5,474,555 A | 12/1995 | Puno et al. |
| 5,476,462 A | 12/1995 | Allard et al. |
| 5,476,464 A | 12/1995 | Metz-Stavenhagen et al. |
| 5,480,401 A | 1/1996 | Navas |
| 5,487,742 A | 1/1996 | Cotrel |
| 5,489,307 A | 2/1996 | Kuslich et al. |
| 5,490,750 A | 2/1996 | Gundy |
| 5,496,321 A | 3/1996 | Puno |
| 5,499,892 A | 3/1996 | Reed |
| 5,507,745 A | 4/1996 | Logroscino et al. |
| 5,540,688 A | 7/1996 | Navas |
| 5,545,165 A | 8/1996 | Biedermann et al. |
| 5,554,157 A | 9/1996 | Errico et al. |
| 5,562,660 A | 10/1996 | Grob |
| 5,562,663 A | 10/1996 | Wisnewski et al. |
| 5,569,247 A | 10/1996 | Morrison |
| 5,569,251 A | 10/1996 | Baker et al. |
| 5,584,834 A | 12/1996 | Errico et al. |
| 5,586,984 A | 12/1996 | Errico et al. |
| 5,591,166 A | 1/1997 | Bernhardt et al. |
| 5,601,553 A | 2/1997 | Trebing et al. |
| 5,607,304 A | 3/1997 | Bailey et al. |
| 5,607,425 A | 3/1997 | Rogozinski |
| 5,607,426 A | 3/1997 | Ralph et al. |
| 5,607,428 A | 3/1997 | Lin |
| 5,611,800 A | 3/1997 | Davis et al. |
| 5,628,740 A | 5/1997 | Mullane |
| 5,630,817 A | 5/1997 | Rokegem |
| 5,641,256 A | 6/1997 | Gundy |
| 5,643,260 A | 7/1997 | Doherty |
| 5,662,652 A | 9/1997 | Schafer et al. |
| 5,662,653 A | 9/1997 | Songer et al. |
| 5,669,909 A | 9/1997 | Zdeblick et al. |
| 5,669,911 A | 9/1997 | Errico et al. |
| 5,672,175 A | 9/1997 | Martin |
| 5,672,176 A | 9/1997 | Biedermann et al. |
| 5,681,319 A | 10/1997 | Biedermann et al. |
| 5,683,390 A | 11/1997 | Metz-Stavenhagen et al. |
| 5,690,630 A | 11/1997 | Errico et al. |
| 5,697,929 A | 12/1997 | Mellinger |
| 5,711,709 A | 1/1998 | McCoy |
| 5,713,898 A | 2/1998 | Stucker et al. |
| 5,716,356 A | 2/1998 | Biedermann et al. |
| 5,723,013 A | 3/1998 | Jeanson et al. |
| 5,725,528 A | 3/1998 | Errico et al. |
| 5,728,098 A | 3/1998 | Sherman et al. |
| 5,733,286 A | 3/1998 | Errico et al. |
| 5,738,685 A | 4/1998 | Halm et al. |
| 5,741,254 A | 4/1998 | Henry et al. |
| 5,752,957 A | 5/1998 | Ralph et al. |
| 5,782,833 A | 7/1998 | Haider |
| 5,797,911 A | 8/1998 | Sherman et al. |
| 5,800,435 A | 9/1998 | Errico et al. |
| 5,800,547 A | 9/1998 | Schafer et al. |
| 5,876,402 A | 3/1999 | Errico et al. |
| 5,879,350 A | 3/1999 | Sherman et al. |
| 5,879,351 A | 3/1999 | Viart |
| 5,882,350 A | 3/1999 | Ralph et al. |
| 5,885,286 A | 3/1999 | Sherman et al. |
| 5,891,145 A | 4/1999 | Morrison et al. |
| RE36,221 E | 6/1999 | Breard et al. |
| 5,944,465 A | 8/1999 | Janitzki |
| 5,951,553 A | 9/1999 | Betz |
| 5,954,725 A | 9/1999 | Sherman et al. |
| 5,961,517 A | 10/1999 | Biedermann et al. |
| 5,964,760 A | 10/1999 | Richelsoph |
| 6,001,098 A | 12/1999 | Metz-Stavenhagen et al. |
| 6,004,349 A | 12/1999 | Jackson |
| 6,010,503 A | 1/2000 | Richelsoph et al. |
| 6,019,759 A | 2/2000 | Rogozinski |
| 6,022,350 A | 2/2000 | Ganem |
| 6,053,917 A | 4/2000 | Sherman et al. |
| 6,059,786 A | 5/2000 | Jackson |
| 6,063,090 A | 5/2000 | Schlapfer |
| 6,074,391 A | 6/2000 | Metz-Stavenhagen et al. |
| 6,077,262 A | 6/2000 | Schlapfer et al. |
| 6,086,588 A | 7/2000 | Ameil et al. |
| 6,090,110 A | 7/2000 | Metz-Stavenhagen |
| 6,090,111 A | 7/2000 | Nichols |
| 6,099,528 A | 8/2000 | Saurat |
| 6,102,913 A | 8/2000 | Jackson |
| 6,110,172 A | 8/2000 | Jackson |
| 6,113,601 A | 9/2000 | Tatar |
| 6,117,137 A | 9/2000 | Halm et al. |
| 6,132,431 A | 10/2000 | Nilsson et al. |
| 6,132,432 A | 10/2000 | Richelsoph |
| 6,132,434 A | 10/2000 | Sherman et al. |
| 6,136,002 A | 10/2000 | Shih et al. |
| 6,143,032 A | 11/2000 | Schafer et al. |
| 6,146,383 A | 11/2000 | Studer et al. |
| 6,183,472 B1 | 2/2001 | Lutz |
| RE37,161 E | 5/2001 | Michelson et al. |
| 6,224,598 B1 | 5/2001 | Jackson |
| 6,235,034 B1 | 5/2001 | Bray |
| 6,241,730 B1 | 6/2001 | Alby |
| 6,248,105 B1 | 6/2001 | Schlapfer et al. |
| 6,254,146 B1 | 7/2001 | Church |
| 6,254,602 B1 | 7/2001 | Justis |
| 6,267,764 B1 | 7/2001 | Elberg |
| 6,267,765 B1 | 7/2001 | Taylor et al. |
| 6,273,888 B1 | 8/2001 | Justis |
| 6,280,442 B1 | 8/2001 | Barker et al. |
| 6,280,445 B1 | 8/2001 | Morrison et al. |
| 6,287,308 B1 | 9/2001 | Betz et al. |
| 6,287,311 B1 | 9/2001 | Sherman et al. |
| 6,296,642 B1 | 10/2001 | Morrison et al. |
| 6,296,643 B1 | 10/2001 | Hopf et al. |
| 6,299,613 B1 | 10/2001 | Ogilvie et al. |

(56) References Cited

U.S. PATENT DOCUMENTS

| | | |
|---|---|---|
| 6,302,888 B1 | 10/2001 | Mellinger et al. |
| 6,309,391 B1 | 10/2001 | Crandall et al. |
| 6,315,564 B1 | 11/2001 | Levisman |
| 6,331,179 B1 | 12/2001 | Freid et al. |
| 6,355,040 B1 | 3/2002 | Richelsoph et al. |
| RE37,665 E | 4/2002 | Ralph et al. |
| 6,368,321 B1 | 4/2002 | Jackson |
| 6,402,752 B2 | 6/2002 | Schaffler-Wachter et al. |
| 6,402,757 B1 | 6/2002 | Moore et al. |
| 6,440,137 B1 | 8/2002 | Horvath et al. |
| 6,451,021 B1 | 9/2002 | Ralph et al. |
| 6,471,703 B1 | 10/2002 | Ashman |
| 6,471,705 B1 | 10/2002 | Biedermann et al. |
| 6,485,491 B1 | 11/2002 | Farris et al. |
| 6,485,492 B1 | 11/2002 | Halm et al. |
| 6,485,494 B1 | 11/2002 | Haider |
| 6,488,681 B2 | 12/2002 | Martin et al. |
| 6,508,818 B2 | 1/2003 | Steiner et al. |
| 6,520,962 B1 | 2/2003 | Taylor et al. |
| 6,527,804 B1 | 3/2003 | Gauchet et al. |
| 6,530,929 B1 | 3/2003 | Justis et al. |
| 6,533,786 B1 | 3/2003 | Needham et al. |
| 6,540,749 B2 | 4/2003 | Schafer et al. |
| 6,547,790 B2 | 4/2003 | Harkey, III et al. |
| 6,551,320 B2 | 4/2003 | Liebermann |
| 6,551,323 B2 | 4/2003 | Doubler et al. |
| 6,554,831 B1 | 4/2003 | Rivard et al. |
| 6,554,832 B2 | 4/2003 | Shluzas |
| 6,554,834 B1 | 4/2003 | Crozet et al. |
| 6,558,387 B2 | 5/2003 | Errico et al. |
| 6,562,040 B1 | 5/2003 | Wagner |
| 6,565,565 B1 | 5/2003 | Yuan et al. |
| 6,582,436 B2 | 6/2003 | Schlapfer et al. |
| 6,582,466 B1 | 6/2003 | Gauchet |
| 6,585,740 B2 | 7/2003 | Schlapfer et al. |
| 6,595,992 B1 | 7/2003 | Wagner et al. |
| 6,595,993 B2 | 7/2003 | Donno et al. |
| 6,610,063 B2 | 8/2003 | Kumar et al. |
| 6,613,050 B1 | 9/2003 | Wagner et al. |
| 6,623,485 B2 | 9/2003 | Doubler et al. |
| 6,626,907 B2 | 9/2003 | Campbell et al. |
| 6,626,908 B2 | 9/2003 | Cooper et al. |
| 6,635,059 B2 | 10/2003 | Randall et al. |
| 6,648,885 B1 | 11/2003 | Friesem |
| 6,648,887 B2 | 11/2003 | Ashman |
| 6,648,888 B1 | 11/2003 | Shluzas |
| 6,652,765 B1 | 11/2003 | Beaty |
| 6,656,179 B1 | 12/2003 | Schaefer et al. |
| 6,656,181 B2 | 12/2003 | Dixon et al. |
| 6,660,004 B2 | 12/2003 | Barker et al. |
| 6,663,632 B1 | 12/2003 | Frigg |
| 6,663,635 B2 | 12/2003 | Frigg et al. |
| 6,673,073 B1 | 1/2004 | Schafer |
| 6,676,661 B1 | 1/2004 | Benlloch et al. |
| 6,679,833 B2 | 1/2004 | Smith et al. |
| 6,682,529 B2 | 1/2004 | Stahurski |
| 6,682,530 B2 | 1/2004 | Dixon et al. |
| 6,689,133 B2 | 2/2004 | Morrison et al. |
| 6,689,134 B2 | 2/2004 | Ralph et al. |
| 6,695,843 B2 | 2/2004 | Biedermann et al. |
| 6,695,851 B2 | 2/2004 | Zdeblick et al. |
| 6,699,249 B2 | 3/2004 | Schlapfer et al. |
| 6,706,045 B2 | 3/2004 | Lin et al. |
| 6,712,818 B1 | 3/2004 | Michelson |
| 6,716,213 B2 | 4/2004 | Shitoto |
| 6,716,214 B1 | 4/2004 | Jackson |
| 6,716,247 B2 | 4/2004 | Michelson |
| 6,723,100 B2 | 4/2004 | Biedermann et al. |
| 6,730,093 B2 | 5/2004 | Saint Martin |
| 6,730,127 B2 | 5/2004 | Michelson |
| 6,733,502 B2 | 5/2004 | Altarac et al. |
| 6,736,816 B2 | 5/2004 | Ritland |
| 6,736,820 B2 | 5/2004 | Biedermann et al. |
| 6,740,086 B2 | 5/2004 | Richelsoph |
| 6,746,449 B2 | 6/2004 | Jones et al. |
| 6,755,829 B1 | 6/2004 | Bono et al. |
| 6,755,835 B2 | 6/2004 | Schultheiss et al. |
| 6,755,836 B1 | 6/2004 | Lewis |
| 6,761,723 B2 | 7/2004 | Buttermann et al. |
| 6,767,351 B2 | 7/2004 | Orbay et al. |
| 6,770,075 B2 | 8/2004 | Howland |
| 6,780,186 B2 | 8/2004 | Errico et al. |
| 6,783,527 B2 | 8/2004 | Drewry et al. |
| 6,790,209 B2 | 9/2004 | Beale et al. |
| 6,802,844 B2 | 10/2004 | Ferree |
| 6,827,719 B2 | 12/2004 | Ralph et al. |
| 6,830,571 B2 | 12/2004 | Lenke et al. |
| 6,835,196 B2 | 12/2004 | Biedermann et al. |
| 6,837,889 B2 | 1/2005 | Shluzas |
| 6,840,940 B2 | 1/2005 | Ralph et al. |
| 6,843,791 B2 | 1/2005 | Serhan |
| 6,858,031 B2 | 2/2005 | Morrison et al. |
| 6,869,432 B2 | 3/2005 | Schlapfer et al. |
| 6,869,433 B2 | 3/2005 | Glascott |
| 6,872,208 B1 | 3/2005 | McBride et al. |
| 6,896,676 B2 | 5/2005 | Zubok et al. |
| 6,932,817 B2 | 8/2005 | Baynham et al. |
| 6,932,820 B2 | 8/2005 | Osman |
| 6,945,972 B2 | 9/2005 | Frigg et al. |
| 6,953,462 B2 | 10/2005 | Lieberman |
| 6,955,677 B2 | 10/2005 | Dahners |
| 6,958,065 B2 | 10/2005 | Ueyama et al. |
| 6,964,664 B2 | 11/2005 | Freid et al. |
| 6,964,665 B2 | 11/2005 | Thomas et al. |
| 6,964,667 B2 | 11/2005 | Shaolian et al. |
| 6,966,910 B2 | 11/2005 | Ritland |
| 6,974,460 B2 | 12/2005 | Carbone et al. |
| 6,979,334 B2 | 12/2005 | Dalton |
| 6,981,973 B2 | 1/2006 | McKinley |
| 6,986,771 B2 | 1/2006 | Paul et al. |
| 6,989,011 B2 | 1/2006 | Paul et al. |
| 6,991,632 B2 | 1/2006 | Ritland |
| RE39,035 E | 3/2006 | Finn et al. |
| 7,008,424 B2 | 3/2006 | Teitelbaum |
| 7,018,378 B2 | 3/2006 | Biedermann et al. |
| 7,018,379 B2 | 3/2006 | Drewry et al. |
| 7,029,475 B2 | 4/2006 | Panjabi |
| 7,125,410 B2 | 10/2006 | Freudiger |
| 7,137,985 B2 | 11/2006 | Jahng |
| 7,207,992 B2 | 4/2007 | Ritland |
| 7,229,441 B2 | 6/2007 | Trieu et al. |
| 7,294,129 B2 | 11/2007 | Hawkins et al. |
| 7,329,258 B2 | 2/2008 | Studer |
| 7,361,196 B2 | 4/2008 | Fallin et al. |
| 7,377,921 B2 | 5/2008 | Studer et al. |
| 8,029,544 B2 * | 10/2011 | Hestad et al. .............. 606/254 |
| 2001/0001119 A1 | 5/2001 | Lombardo |
| 2001/0010000 A1 | 7/2001 | Gertzbein |
| 2001/0029375 A1 | 10/2001 | Betz |
| 2001/0037111 A1 | 11/2001 | Dixon et al. |
| 2002/0007184 A1 | 1/2002 | Ogilvie et al. |
| 2002/0013586 A1 | 1/2002 | Justis et al. |
| 2002/0035366 A1 | 3/2002 | Walder et al. |
| 2002/0045898 A1 | 4/2002 | Freid et al. |
| 2002/0058942 A1 | 5/2002 | Biedermann et al. |
| 2002/0082602 A1 | 6/2002 | Biedermann et al. |
| 2002/0111626 A1 | 8/2002 | Ralph et al. |
| 2002/0143341 A1 | 10/2002 | Biedermann et al. |
| 2002/0173789 A1 | 11/2002 | Howland |
| 2002/0193795 A1 | 12/2002 | Gertzbein et al. |
| 2003/0023243 A1 | 1/2003 | Biedermann et al. |
| 2003/0073996 A1 | 4/2003 | Doubler et al. |
| 2003/0083657 A1 | 5/2003 | Drewry et al. |
| 2003/0093078 A1 | 5/2003 | Ritland |
| 2003/0100896 A1 | 5/2003 | Biedermann et al. |
| 2003/0105460 A1 | 6/2003 | Crandall et al. |
| 2003/0109880 A1 | 6/2003 | Shirado et al. |
| 2003/0114852 A1 | 6/2003 | Biedermann et al. |
| 2003/0125741 A1 | 7/2003 | Biedermann et al. |
| 2003/0149432 A1 | 8/2003 | Frigg et al. |
| 2003/0163133 A1 | 8/2003 | Altarac et al. |
| 2003/0171749 A1 | 9/2003 | Le Douedic et al. |
| 2003/0176862 A1 | 9/2003 | Taylor et al. |
| 2003/0191470 A1 | 10/2003 | Ritland |

(56) References Cited

U.S. PATENT DOCUMENTS

| | | |
|---|---|---|
| 2003/0199873 A1 | 10/2003 | Richelsoph |
| 2003/0208204 A1 | 11/2003 | Bailey et al. |
| 2003/0216735 A1 | 11/2003 | Altarac et al. |
| 2003/0220642 A1 | 11/2003 | Freudiger |
| 2003/0220643 A1 | 11/2003 | Ferree |
| 2004/0002708 A1 | 1/2004 | Ritland |
| 2004/0006342 A1 | 1/2004 | Altarac et al. |
| 2004/0049189 A1 | 3/2004 | Le Couedic et al. |
| 2004/0049190 A1 | 3/2004 | Biedermann et al. |
| 2004/0073215 A1 | 4/2004 | Carti |
| 2004/0078082 A1 | 4/2004 | Lange |
| 2004/0087949 A1 | 5/2004 | Bono et al. |
| 2004/0087952 A1 | 5/2004 | Borgstrom et al. |
| 2004/0092934 A1 | 5/2004 | Howland |
| 2004/0097933 A1 | 5/2004 | Lourdel et al. |
| 2004/0116929 A1 | 6/2004 | Barker et al. |
| 2004/0138662 A1 | 7/2004 | Landry et al. |
| 2004/0143265 A1 | 7/2004 | Landry et al. |
| 2004/0147928 A1 | 7/2004 | Landry et al. |
| 2004/0147929 A1 | 7/2004 | Biedermann et al. |
| 2004/0158247 A1 | 8/2004 | Sitiso et al. |
| 2004/0172022 A1 | 9/2004 | Landry et al. |
| 2004/0176766 A1 | 9/2004 | Shluzas |
| 2004/0186473 A1 | 9/2004 | Cournoyer et al. |
| 2004/0210216 A1 | 10/2004 | Farris et al. |
| 2004/0225289 A1 | 11/2004 | Biedermann et al. |
| 2004/0236327 A1 | 11/2004 | Paul et al. |
| 2004/0236328 A1 | 11/2004 | Paul et al. |
| 2004/0236329 A1 | 11/2004 | Panjabi |
| 2004/0236330 A1 | 11/2004 | Purcell et al. |
| 2004/0249380 A1 | 12/2004 | Glascott |
| 2004/0260283 A1 | 12/2004 | Wu et al. |
| 2004/0267264 A1 | 12/2004 | Konieczynski et al. |
| 2005/0027296 A1 | 2/2005 | Thramann et al. |
| 2005/0033298 A1 | 2/2005 | Hawkes et al. |
| 2005/0038432 A1 | 2/2005 | Shaolian et al. |
| 2005/0049708 A1 | 3/2005 | Atkinson et al. |
| 2005/0055026 A1 | 3/2005 | Biedermann et al. |
| 2005/0065515 A1 | 3/2005 | Jahng |
| 2005/0065516 A1 | 3/2005 | Johng |
| 2005/0070899 A1 | 3/2005 | Doubler et al. |
| 2005/0080415 A1 | 4/2005 | Keyer et al. |
| 2005/0085815 A1 | 4/2005 | Harms et al. |
| 2005/0085816 A1 | 4/2005 | Michelson |
| 2005/0096652 A1 | 5/2005 | Burton |
| 2005/0107788 A1 | 5/2005 | Beaurain et al. |
| 2005/0113927 A1 | 5/2005 | Malek |
| 2005/0124991 A1 | 6/2005 | Jahng |
| 2005/0131404 A1 | 6/2005 | Mazda et al. |
| 2005/0131407 A1 | 6/2005 | Sicvol et al. |
| 2005/0131413 A1 | 6/2005 | O'Driscoll et al. |
| 2005/0137597 A1 | 6/2005 | Butler et al. |
| 2005/0143737 A1 | 6/2005 | Pafford et al. |
| 2005/0143823 A1 | 6/2005 | Boyd et al. |
| 2005/0149020 A1 | 7/2005 | Jahng |
| 2005/0149023 A1 | 7/2005 | Ritland |
| 2005/0154389 A1 | 7/2005 | Selover et al. |
| 2005/0154390 A1 | 7/2005 | Biedermann et al. |
| 2005/0154391 A1 | 7/2005 | Doherty et al. |
| 2005/0159750 A1 | 7/2005 | Doherty |
| 2005/0165396 A1 | 7/2005 | Fortin et al. |
| 2005/0165400 A1 | 7/2005 | Fernandez |
| 2005/0171540 A1 | 8/2005 | Lim et al. |
| 2005/0171543 A1 | 8/2005 | Timm et al. |
| 2005/0177157 A1 | 8/2005 | Jahng |
| 2005/0182401 A1 | 8/2005 | Timm et al. |
| 2005/0187548 A1 | 8/2005 | Butler et al. |
| 2005/0187555 A1 | 8/2005 | Biedermann et al. |
| 2005/0192580 A1 | 9/2005 | Dalton |
| 2005/0203511 A1 | 9/2005 | Wilson-MacDonald et al. |
| 2005/0203513 A1 | 9/2005 | Jahng et al. |
| 2005/0203514 A1 | 9/2005 | Jahng et al. |
| 2005/0203516 A1 | 9/2005 | Biedermann et al. |
| 2005/0203517 A1 | 9/2005 | Jahng et al. |
| 2005/0203518 A1 | 9/2005 | Biedermann et al. |
| 2005/0203519 A1 | 9/2005 | Harms et al. |
| 2005/0216001 A1 | 9/2005 | David |
| 2005/0216003 A1 | 9/2005 | Biedermann et al. |
| 2005/0228501 A1 | 10/2005 | Miller et al. |
| 2005/0234450 A1 | 10/2005 | Barker |
| 2005/0234451 A1 | 10/2005 | Markworth |
| 2005/0234452 A1 | 10/2005 | Malandain |
| 2005/0234453 A1 | 10/2005 | Shaolian et al. |
| 2005/0234454 A1 | 10/2005 | Chin |
| 2005/0234456 A1 | 10/2005 | Malandain |
| 2005/0240181 A1 | 10/2005 | Boomer et al. |
| 2005/0240183 A1 | 10/2005 | Vaughan |
| 2005/0245930 A1 | 11/2005 | Timm et al. |
| 2005/0251137 A1 | 11/2005 | Ball |
| 2005/0251140 A1 | 11/2005 | Shaolian et al. |
| 2005/0251141 A1 | 11/2005 | Frigg et al. |
| 2005/0261685 A1 | 11/2005 | Fortin et al. |
| 2005/0261687 A1 | 11/2005 | Garamszegi et al. |
| 2005/0267470 A1 | 12/2005 | McBride |
| 2005/0267471 A1 | 12/2005 | Biedermann et al. |
| 2005/0267474 A1 | 12/2005 | Dalton |
| 2005/0273099 A1 | 12/2005 | Baccelli et al. |
| 2005/0273101 A1 | 12/2005 | Schumacher |
| 2005/0277919 A1 | 12/2005 | Slivka et al. |
| 2005/0277922 A1 | 12/2005 | Trieu et al. |
| 2005/0277923 A1 | 12/2005 | Sweeney |
| 2005/0277925 A1 | 12/2005 | Mujwid |
| 2005/0277927 A1 | 12/2005 | Guenther et al. |
| 2005/0277928 A1 | 12/2005 | Boschert |
| 2005/0277932 A1* | 12/2005 | Farris ............................ 606/61 |
| 2005/0283152 A1 | 12/2005 | Lindemann et al. |
| 2005/0283157 A1 | 12/2005 | Coates et al. |
| 2005/0283238 A1 | 12/2005 | Reiley |
| 2005/0283244 A1 | 12/2005 | Gordon et al. |
| 2005/0288669 A1 | 12/2005 | Abdou |
| 2005/0288670 A1 | 12/2005 | Panjabi et al. |
| 2005/0288671 A1 | 12/2005 | Yuan et al. |
| 2005/0288672 A1 | 12/2005 | Ferree |
| 2005/0288673 A1 | 12/2005 | Catbagan et al. |
| 2006/0004357 A1 | 1/2006 | Lee et al. |
| 2006/0004359 A1 | 1/2006 | Kramer et al. |
| 2006/0004360 A1 | 1/2006 | Kramer et al. |
| 2006/0004363 A1 | 1/2006 | Brockmeyer et al. |
| 2006/0009767 A1 | 1/2006 | Kiester |
| 2006/0009768 A1 | 1/2006 | Ritland |
| 2006/0009769 A1 | 1/2006 | Lieberman |
| 2006/0009770 A1 | 1/2006 | Speirs et al. |
| 2006/0009846 A1 | 1/2006 | Trieu et al. |
| 2006/0015099 A1 | 1/2006 | Cannon et al. |
| 2006/0015104 A1 | 1/2006 | Dalton |
| 2006/0025767 A1 | 2/2006 | Khalili |
| 2006/0025768 A1 | 2/2006 | Iott et al. |
| 2006/0025770 A1 | 2/2006 | Schlapfer et al. |
| 2006/0036240 A1 | 2/2006 | Colleran et al. |
| 2006/0036242 A1 | 2/2006 | Nilsson et al. |
| 2006/0036244 A1 | 2/2006 | Spitler et al. |
| 2006/0036246 A1 | 2/2006 | Carl et al. |
| 2006/0036252 A1 | 2/2006 | Baynham et al. |
| 2006/0036256 A1 | 2/2006 | Carl et al. |
| 2006/0036259 A1 | 2/2006 | Carl et al. |
| 2006/0036323 A1 | 2/2006 | Carl et al. |
| 2006/0036324 A1 | 2/2006 | Sachs et al. |
| 2006/0041259 A1 | 2/2006 | Paul et al. |
| 2006/0052780 A1 | 3/2006 | Errico et al. |
| 2006/0052783 A1 | 3/2006 | Dant et al. |
| 2006/0052784 A1 | 3/2006 | Dant et al. |
| 2006/0052786 A1 | 3/2006 | Dant et al. |
| 2006/0058788 A1 | 3/2006 | Hammer et al. |
| 2006/0058790 A1 | 3/2006 | Carl et al. |
| 2006/0064090 A1 | 3/2006 | Park |
| 2006/0064091 A1 | 3/2006 | Ludwig et al. |
| 2006/0064092 A1 | 3/2006 | Howland |
| 2006/0069390 A1 | 3/2006 | Frigg |
| 2006/0079896 A1 | 4/2006 | Kwak |
| 2006/0079898 A1 | 4/2006 | Ainsworth |
| 2006/0084982 A1 | 4/2006 | Kim |
| 2006/0084983 A1 | 4/2006 | Kim |
| 2006/0084984 A1 | 4/2006 | Kim |
| 2006/0084985 A1 | 4/2006 | Kim |

(56) References Cited

U.S. PATENT DOCUMENTS

| | | |
|---|---|---|
| 2006/0084987 A1 | 4/2006 | Kim |
| 2006/0084988 A1 | 4/2006 | Kim |
| 2006/0084991 A1 | 4/2006 | Borgstrom |
| 2006/0085069 A1 | 4/2006 | Kim |
| 2006/0106381 A1 | 5/2006 | Ferree |
| 2006/0122599 A1 | 6/2006 | Drewry |
| 2006/0129239 A1 | 6/2006 | Kwak |
| 2006/0142758 A1 | 6/2006 | Petit |
| 2006/0142760 A1 | 6/2006 | McDonnell |
| 2006/0149228 A1 | 7/2006 | Schlapfer |
| 2006/0149229 A1 | 7/2006 | Kwak |
| 2006/0184171 A1 | 8/2006 | Biedermann |
| 2006/0184180 A1 | 8/2006 | Augostino |
| 2006/0189983 A1 | 8/2006 | Fallin |
| 2006/0189984 A1 | 8/2006 | Fallin |
| 2006/0189985 A1 | 8/2006 | Lewis |
| 2006/0195090 A1 | 8/2006 | Suddaby |
| 2006/0195093 A1 | 8/2006 | Jahng |
| 2006/0200130 A1 | 9/2006 | Hawkins |
| 2006/0212033 A1 | 9/2006 | Rothman |
| 2006/0229608 A1 | 10/2006 | Foster |
| 2006/0229609 A1 | 10/2006 | Wang |
| 2006/0229612 A1 | 10/2006 | Rothman |
| 2006/0229613 A1 | 10/2006 | Timm |
| 2006/0241603 A1 | 10/2006 | Jackson |
| 2006/0241769 A1 | 10/2006 | Gordon |
| 2006/0241771 A1 | 10/2006 | Gordon |
| 2006/0247632 A1 | 11/2006 | Winslow |
| 2006/0247633 A1 | 11/2006 | Winslow |
| 2006/0247635 A1 | 11/2006 | Gordon |
| 2006/0247637 A1 | 11/2006 | Colleran |
| 2006/0247779 A1 | 11/2006 | Gordon |
| 2006/0264935 A1 | 11/2006 | White |
| 2006/0264937 A1* | 11/2006 | White ............................ 606/61 |
| 2006/0264940 A1 | 11/2006 | Hartmannt |
| 2006/0282075 A1 | 12/2006 | Labrom |
| 2006/0282076 A1 | 12/2006 | Labrom |
| 2006/0282077 A1 | 12/2006 | Labrom |
| 2006/0282078 A1 | 12/2006 | Labrom |
| 2006/0282079 A1 | 12/2006 | Labrom |
| 2006/0282080 A1 | 12/2006 | Albert |
| 2006/0293657 A1 | 12/2006 | Hartmann |
| 2006/0293663 A1 | 12/2006 | Walkenhorst |
| 2007/0005062 A1 | 1/2007 | Lange |
| 2007/0005063 A1 | 1/2007 | Bruneau |
| 2007/0005137 A1 | 1/2007 | Kwak |
| 2007/0016190 A1 | 1/2007 | Martinez |
| 2007/0016193 A1 | 1/2007 | Ritland |
| 2007/0043356 A1 | 2/2007 | Timm |
| 2007/0049936 A1 | 3/2007 | Colleran |
| 2007/0055236 A1 | 3/2007 | Hudgins |
| 2007/0055247 A1 | 3/2007 | Jahng |
| 2007/0073289 A1 | 3/2007 | Kwak |
| 2007/0073293 A1 | 3/2007 | Martz |
| 2007/0078461 A1 | 4/2007 | Shluzas |
| 2007/0088359 A1 | 4/2007 | Woods et al. |
| 2007/0093813 A1 | 4/2007 | Callahan, II et al. |
| 2007/0093814 A1 | 4/2007 | Callahan, II et al. |
| 2007/0093815 A1 | 4/2007 | Callahan, II et al. |
| 2007/0100341 A1* | 5/2007 | Reglos et al. ................... 606/61 |
| 2007/0118119 A1 | 5/2007 | Hestad |
| 2007/0118122 A1 | 5/2007 | Butler et al. |
| 2007/0123864 A1 | 5/2007 | Walder et al. |
| 2007/0123865 A1 | 5/2007 | Schlapfer et al. |
| 2007/0123866 A1 | 5/2007 | Gerbec et al. |
| 2007/0123871 A1 | 5/2007 | Jahng |
| 2007/0129729 A1 | 6/2007 | Petit et al. |
| 2007/0135815 A1 | 6/2007 | Gerbec et al. |
| 2007/0161991 A1 | 7/2007 | Altarac et al. |
| 2007/0161997 A1 | 7/2007 | Thramann et al. |
| 2007/0173818 A1 | 7/2007 | Hestad et al. |
| 2007/0173822 A1 | 7/2007 | Bruneau et al. |
| 2007/0173832 A1 | 7/2007 | Tebbe et al. |
| 2007/0191841 A1 | 8/2007 | Justis et al. |
| 2007/0191846 A1 | 8/2007 | Bruneau et al. |
| 2007/0123720 A1 | 9/2007 | Gordon et al. |
| 2007/0225708 A1 | 9/2007 | Biedermann et al. |
| 2007/0225710 A1 | 9/2007 | Jahng et al. |
| 2007/0233064 A1 | 10/2007 | Holt |
| 2007/0233073 A1 | 10/2007 | Wisnewski et al. |
| 2007/0233075 A1 | 10/2007 | Dawson |
| 2007/0233085 A1 | 10/2007 | Biedermann et al. |
| 2007/0233087 A1 | 10/2007 | Schlapfer |
| 2007/0233092 A1 | 10/2007 | Falahee |
| 2007/0233094 A1 | 10/2007 | Colleran et al. |
| 2007/0233095 A1 | 10/2007 | Schlaepfer |
| 2007/0124249 A1 | 11/2007 | Aerrabotu et al. |
| 2007/0270814 A1* | 11/2007 | Lim et al. ........................ 606/61 |
| 2007/0270821 A1* | 11/2007 | Trieu et al. ..................... 606/61 |
| 2007/0270837 A1 | 11/2007 | Eckhardt et al. |
| 2007/0270838 A1 | 11/2007 | Bruneau et al. |
| 2007/0270843 A1 | 11/2007 | Matthis et al. |
| 2007/0276380 A1 | 11/2007 | Jahng et al. |
| 2007/0288008 A1 | 12/2007 | Park |
| 2007/0288009 A1 | 12/2007 | Brown et al. |
| 2007/0288011 A1 | 12/2007 | Logan |
| 2007/0288012 A1 | 12/2007 | Colleran et al. |
| 2008/0021458 A1 | 1/2008 | Lim |
| 2008/0021459 A1 | 1/2008 | Lim |
| 2008/0021462 A1 | 1/2008 | Trieu |
| 2008/0021464 A1 | 1/2008 | Morin et al. |
| 2008/0021465 A1 | 1/2008 | Shadduck et al. |
| 2008/0021466 A1 | 1/2008 | Shadduck et al. |
| 2008/0033435 A1 | 2/2008 | Studer et al. |
| 2008/0039843 A1 | 2/2008 | Abdou |
| 2008/0045951 A1 | 2/2008 | Fanger et al. |
| 2008/0051787 A1 | 2/2008 | Remington et al. |
| 2008/0058812 A1 | 3/2008 | Zehnder |
| 2008/0065071 A1 | 3/2008 | Park |
| 2008/0065073 A1 | 3/2008 | Perriello et al. |
| 2008/0065077 A1 | 3/2008 | Ferree |
| 2008/0065079 A1 | 3/2008 | Bruneau et al. |
| 2008/0071273 A1 | 3/2008 | Hawkes et al. |
| 2008/0071274 A1 | 3/2008 | Ensign |
| 2008/0091214 A1 | 4/2008 | Richelsoph |
| 2008/0097431 A1 | 4/2008 | Vessa |
| 2008/0097434 A1 | 4/2008 | Moumene et al. |
| 2008/0097441 A1 | 4/2008 | Hayes et al. |
| 2008/0125777 A1 | 5/2008 | Veldman et al. |
| 2008/0125787 A1 | 5/2008 | Doubler et al. |
| 2008/0140133 A1 | 6/2008 | Allard et al. |
| 2008/0154307 A1 | 6/2008 | Colleran et al. |
| 2008/0154308 A1 | 6/2008 | Sherman et al. |
| 2008/0161854 A1 | 7/2008 | Bae et al. |
| 2008/0167687 A1 | 7/2008 | Colleran et al. |
| 2008/0177316 A1 | 7/2008 | Bergeronk et al. |
| 2008/0177319 A1 | 7/2008 | Schwab |
| 2008/0177327 A1 | 7/2008 | Malandain et al. |
| 2008/0183212 A1 | 7/2008 | Veldman et al. |
| 2008/0183213 A1 | 7/2008 | Veldman et al. |
| 2008/0183215 A1 | 7/2008 | Altarac et al. |
| 2008/0195100 A1 | 8/2008 | Capote et al. |

FOREIGN PATENT DOCUMENTS

| | | |
|---|---|---|
| DE | 4425392 | 11/1995 |
| DE | 19507141 | 9/1996 |
| DE | 19509331 | 9/1996 |
| DE | 29806563 | 7/1998 |
| DE | 29810798 | 12/1999 |
| DE | 19951145 | 5/2001 |
| DE | 10236691 | 2/2004 |
| DE | 102007055745 | 7/2008 |
| EP | 0667127 | 8/1995 |
| EP | 0669109 | 8/1995 |
| EP | 0677277 | 10/1995 |
| EP | 0885598 | 12/1998 |
| EP | 1121902 | 8/2001 |
| EP | 1190678 | 3/2002 |
| EP | 1570795 | 2/2005 |
| EP | 1570795 | 9/2005 |
| EP | 1579816 | 9/2005 |
| EP | 1634537 | 3/2006 |
| FR | 2717370 | 9/1995 |

(56) References Cited

FOREIGN PATENT DOCUMENTS

| | | |
|---|---|---|
| FR | 2718946 | 10/1995 |
| FR | 2729291 | 7/1996 |
| FR | 2796545 | 1/2001 |
| FR | 2799949 | 4/2001 |
| FR | 2814936 | 4/2002 |
| FR | 2856578 | 6/2003 |
| FR | 2865373 | 1/2004 |
| FR | 2865375 | 1/2004 |
| FR | 2865377 | 1/2004 |
| FR | 2857850 | 4/2004 |
| FR | 2865378 | 10/2004 |
| GB | 2365345 | 2/2002 |
| GB | 2382304 | 5/2003 |
| JP | 10277070 | 10/1998 |
| JP | 2000325358 | 3/2000 |
| WO | WO92/03100 | 3/1992 |
| WO | WO94/10927 | 5/1994 |
| WO | WO94/26191 | 11/1994 |
| WO | WO9641582 | 12/1996 |
| WO | WO01/45576 | 6/2001 |
| WO | WO02/054966 | 7/2002 |
| WO | WO02/102259 | 12/2002 |
| WO | WO03/026523 | 4/2003 |
| WO | WO03/068088 | 8/2003 |
| WO | WO2004/041100 | 5/2004 |
| WO | WO2004/075778 | 9/2004 |
| WO | WO2004/089245 | 10/2004 |
| WO | WO2004/107997 | 12/2004 |
| WO | WO2005/000136 | 1/2005 |
| WO | WO2005/000137 | 1/2005 |
| WO | WO2005/020829 | 3/2005 |
| WO | WO2005/065374 | 7/2005 |
| WO | WO2005/065375 | 7/2005 |
| WO | WO2005/072632 | 8/2005 |
| WO | WO2005/082262 | 9/2005 |
| WO | WO2005/099400 | 10/2005 |
| WO | WO2005/104969 | 11/2005 |
| WO | WO2006/012088 | 2/2006 |
| WO | WO2006/017616 | 2/2006 |
| WO | WO 2006/028537 | 3/2006 |
| WO | WO2006/045094 | 4/2006 |
| WO | WO2007/002409 | 1/2007 |
| WO | WO2008/069420 | 6/2008 |
| WO | WO2008/088990 | 7/2008 |
| WO | WO2008/089075 | 7/2008 |

OTHER PUBLICATIONS

*Claris Instrumentation* Brochure, G Med, pub. 1997.
*VLS System Variable Locking Screw* Brochure, Interpore Cross International, 1999.
*CD Horizon M8 Multi Axial Screw Spinal System* Brochure, Medtronic Sofamor Danek, no publish date.
*Contour Spinal System* Brochure, Ortho Development, no publish date.
*Xia Spinal System* Brochure, Stryker Howmedica Osteonics, no publish date.
*The Rod Plate System* Brochure, Stryker Howmedica Osteonics, pub. Oct. 1999.
*Silhouette Spinal Fixation System* Brochure, Sulzer Medica Spine-Tech, no publish date.
*SDRS Surgical Dynamics Rod System* Brochure, Surgical Dynamics, pub. 1998-1999.
*Versalok Low Back Fixation System* Brochure, Wright Medical Technology, Inc., pub. 1997.
*The Strength of Innovation* Advertisement, Blackstone Medical Inc., no publish date.
*The Moss Miami 6.0mm System* Advertisement, author unknown, no publish date.
*Spine*, Lipcott, Williams & Wilkins, Inc. vol. 24, No. 15, p. 1495.
Brochure of Tyco/Healthcare/Surgical Dynamics on Spiral Radius 90D, Publication Date: Sep. 2001, pp. 1-8.

\* cited by examiner

DYNAMIC STABILIZATION MEMBER WITH END PLATE SUPPORT AND CABLE CORE EXTENSION

CROSS-REFERENCE TO RELATED APPLICATIONS

This application claims the benefit of U.S. Provisional Patent Application Ser. No. 61/000,955, filed Oct. 30, 2007 and also the benefit of U.S. Provisional Patent Application Ser. No. 60/999,965, filed Oct. 23, 2007, both of which are incorporated by reference herein.

BACKGROUND OF THE INVENTION

The present invention is directed to dynamic fixation assemblies for use in bone surgery, particularly spinal surgery, and in particular to longitudinal connecting members and cooperating bone anchors or fasteners for such assemblies, the connecting members being attached to at least two bone anchors.

Historically, it has been common to fuse adjacent vertebrae that are placed in fixed relation by the installation therealong of bone screws or other bone anchors and cooperating longitudinal connecting members or other elongate members. Fusion results in the permanent immobilization of one or more of the intervertebral joints. Because the anchoring of bone screws, hooks and other types of anchors directly to a vertebra can result in significant forces being placed on the vertebra, and such forces may ultimately result in the loosening of the bone screw or other anchor from the vertebra, fusion allows for the growth and development of a bone counterpart to the longitudinal connecting member that can maintain the spine in the desired position even if the implants ultimately fail or are removed. Because fusion has been a desired component of spinal stabilization procedures, longitudinal connecting members have been designed that are of a material, size and shape to largely resist flexure, extension, torsion, distraction and compression, and thus substantially immobilize the portion of the spine that is to be fused. Thus, longitudinal connecting members are typically uniform along an entire length thereof, and usually made from a single or integral piece of material having a uniform diameter or width of a size to provide substantially rigid support in all planes.

Fusion, however, has some undesirable side effects. One apparent side effect is the immobilization of a portion of the spine. Furthermore, although fusion may result in a strengthened portion of the spine, it also has been linked to more rapid degeneration and even hyper-mobility and collapse of spinal motion segments that are adjacent to the portion of the spine being fused, reducing or eliminating the ability of such spinal joints to move in a more normal relation to one another. In certain instances, fusion has also failed to provide pain relief.

An alternative to fusion and the use of more rigid longitudinal connecting members or other rigid structure has been a "soft" or "dynamic" stabilization approach in which a flexible loop-, S-, C- or U-shaped member or a coil-like and/or a spring-like member is utilized as an elastic longitudinal connecting member fixed between a pair of pedicle screws in an attempt to create, as much as possible, a normal loading pattern between the vertebrae in flexion, extension, distraction, compression, side bending and torsion. Problems may arise with such devices, however, including tissue scarring, lack of adequate spinal support or being undesirably large or bulky when sized to provide adequate support, and lack of fatigue strength or endurance limit. Fatigue strength has been defined as the repeated loading and unloading of a specific stress on a material structure until it fails. Fatigue strength can be tensile or distraction, compression, shear, torsion, bending, or a combination of these.

Another type of soft or dynamic system known in the art includes bone anchors connected by flexible cords or strands, typically made from a plastic material. Such a cord or strand may be threaded through cannulated spacers that are disposed between adjacent bone anchors when such a cord or strand is implanted, tensioned and attached to the bone anchors. The spacers typically span the distance between bone anchors, providing limits on the bending movement of the cord or strand and thus strengthening and supporting the overall system. Such cord or strand-type systems require specialized bone anchors and tooling for tensioning and holding the cord or strand in the bone anchors. Although flexible, the cords or strands utilized in such systems do not allow for elastic distraction of the system once implanted because the cord or strand must be stretched or pulled to maximum tension in order to provide a stable, supportive system. Also, as currently designed, these systems do not provide any significant torsional resistance. Furthermore, such systems allow the possibility for at least some partial pulling away from or gapping between the adjacent bone screw heads and the cannulated spacers, providing space for the growth of soft tissue and scarring that may result in pinching and resultant pain to the patient as well as altered bio-mechanics for the implants.

The complex dynamic conditions associated with spinal movement therefore provide quite a challenge for the design of elongate elastic longitudinal connecting members that exhibit an adequate fatigue strength to provide stabilization and protected motion of the spine, without fusion, and allow for some natural movement of the portion of the spine being reinforced and supported by the elongate elastic or flexible connecting member. A further challenge are situations in which a portion or length of the spine requires a more rigid stabilization, possibly including fusion, while another portion or length may be better supported by a more dynamic system that allows for protective movement.

SUMMARY OF THE INVENTION

Longitudinal connecting member assemblies according to the invention for use between at least two bone anchors provide dynamic, protected motion of the spine and may be extended to provide additional dynamic sections or more rigid support along an adjacent length of the spine, with fusion, if desired. A longitudinal connecting member assembly according to the invention includes first and second elongate segments, each segment having an abutment plate with a plurality of integral fins extending axially from the abutment plate. The fins face one-another and are evenly spaced from one another and are also evenly spaced from the opposing plate. The first connecting member further includes an elongate central inner core extension in the form of a flexible cable or cord that extends axially between the fins and also through the second connecting member. The assembly further includes an elastic molded outer spacer or elastic sleeve substantially or completely disposed about the fins and substantially or completely surrounding each of the plates. The fins may be cupped or hooked to further grab and hold the elastomer. The assembly may further include an optional elastic end bumper that places a distractive force on the elongate inner core. The cooperation between the cupped fins and the elastomeric spacer that may be over-molded around the abutment plates prevents or eliminates gapping or pulling away of the plate from the elastic polymer of the spacer so that soft tissues and body fluids cannot get into such a gap or space, especially when compression is applied on one side of the spacer and resultant distraction on the opposite side, such as when a bending moment is applied to the screws.

OBJECTS AND ADVANTAGES OF THE INVENTION

An object of the invention is to provide dynamic medical implant stabilization assemblies having longitudinal connecting members that include a flexible portion that allows for bending, torsion, compression and distraction of the assembly. Another object of the invention is to provide such a flexible portion that is molded about cooperating rigid portions such that the flexible portion does not pull away or otherwise separate from the rigid portion in response to body movement or other forces. A further object of the invention is to provide dynamic medical implant longitudinal connecting members that may be utilized with a variety of bone screws, hooks and other bone anchors. Another object of the invention is to provide a more rigid or solid connecting member portion or segment, if desired, such as a solid rod portion integral with or connected to the flexible portion. Additionally, it is an object of the invention to provide a lightweight, reduced volume, low profile assembly including at least two bone anchors and a longitudinal connecting member therebetween. Furthermore, it is an object of the invention to provide apparatus and methods that are easy to use and especially adapted for the intended use thereof and wherein the apparatus are comparatively inexpensive to make and suitable for use.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

DETAILED DESCRIPTION OF THE EMBODIMENT

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. It is also noted that any reference to the words top, bottom, up and down, and the like, in this application refers to the alignment shown in the various drawings, as well as the normal connotations applied to such devices, and is not intended to restrict positioning of the connecting member assemblies of the application and cooperating bone anchors in actual use.

With reference to FIGS. 1-7, the reference numeral 1 generally designates a non-fusion dynamic stabilization longitudinal connecting member assembly according to the present invention. The connecting member assembly 1 includes first and second elongate segments, generally 4 and 5, an elastic bumper 6 and a crimping ring 7. The elongate segment 4 further includes an inner core extension 8 in the form of a cable, strap or other flexible cord-like extension. The inner core can be used to pretension the device or simply to help limit elongation with distraction. The assembly further includes an outer sleeve or spacer 10. The illustrated cable core extension 8 includes an elongate body or length 12 and a plug or end portion 13 for inserting and retaining within the segment 4, utilizing a threaded annular tap 14 that abuts against an annular rigid end surface 15 of the plug 13 as will be described in greater detail below. The illustrated core plug 13 is integral with the core body 12. However, it is foreseen that in other embodiments, the plug 13 may be adhered or otherwise fixed to the core body 12. The core cable 8 operationally extends along a longitudinal axis A that is also the central longitudinal axis A of the entire assembly 1 when the spacer 10 is molded thereon, connecting the segments 4 and 5. Again, the core 8 may be pre-tensioned, providing additional stability to the assembly 1. The core 8 may be tensioned prior to and/or after molding of the spacer 10.

Figure 1:
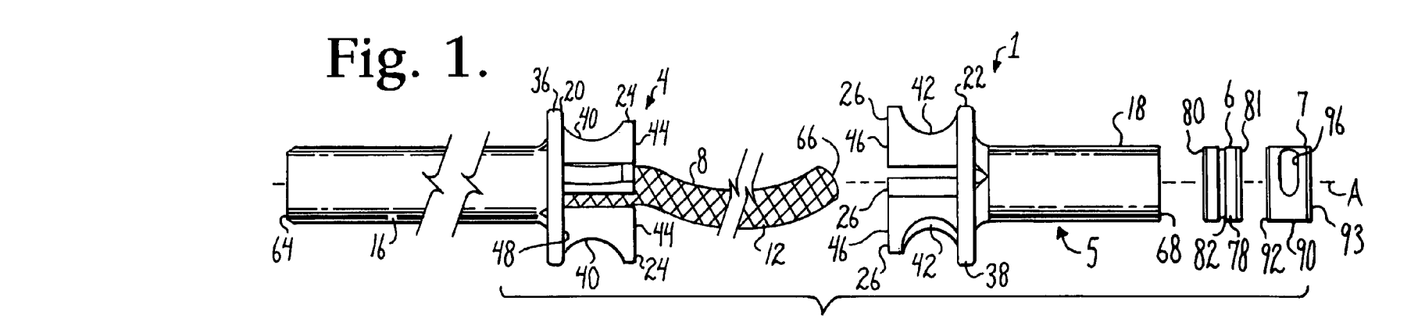
FIG. 1 is an enlarged and exploded front elevational view of a dynamic fixation connecting member assembly according to the invention including first and second elongate members, each with a finned plate, an elongate, core cable fixed to the first member, an elastic bumper, a crimping ring and an outer molded spacer (not shown).
Figure 2:
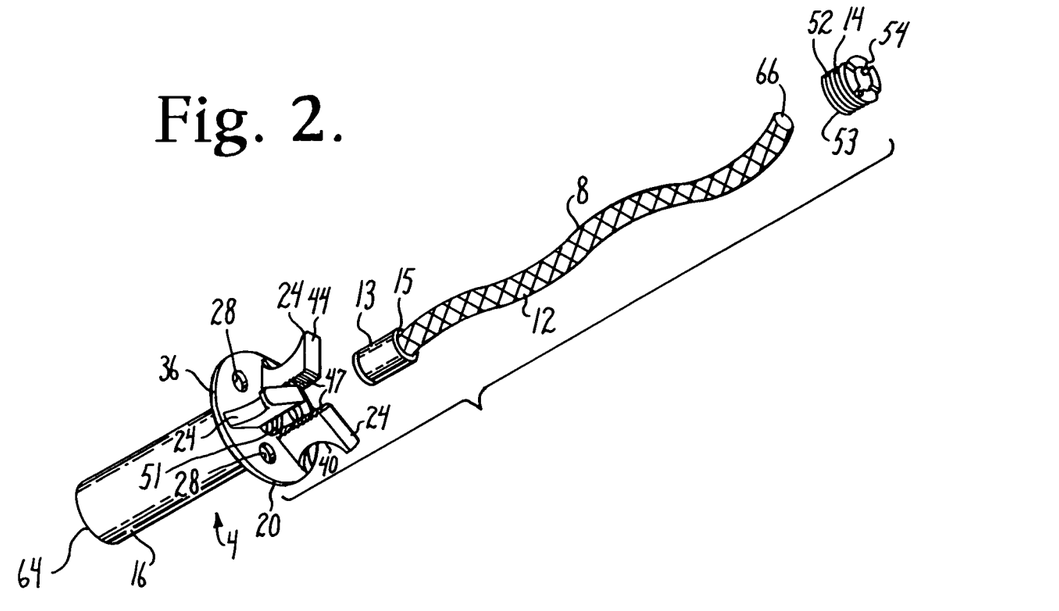
FIG. 2 is a reduced exploded perspective view of the first elongate member and the core cable of FIG. 1, also showing a cooperating attachment member.
Figure 3:
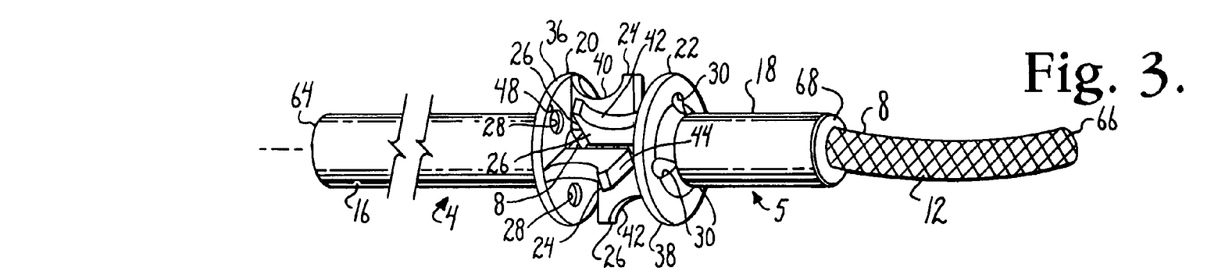
FIG. 3 is an enlarged perspective view of the assembly of FIG. 1 without the bumper, crimping ring and molded spacer.
Figure 4:
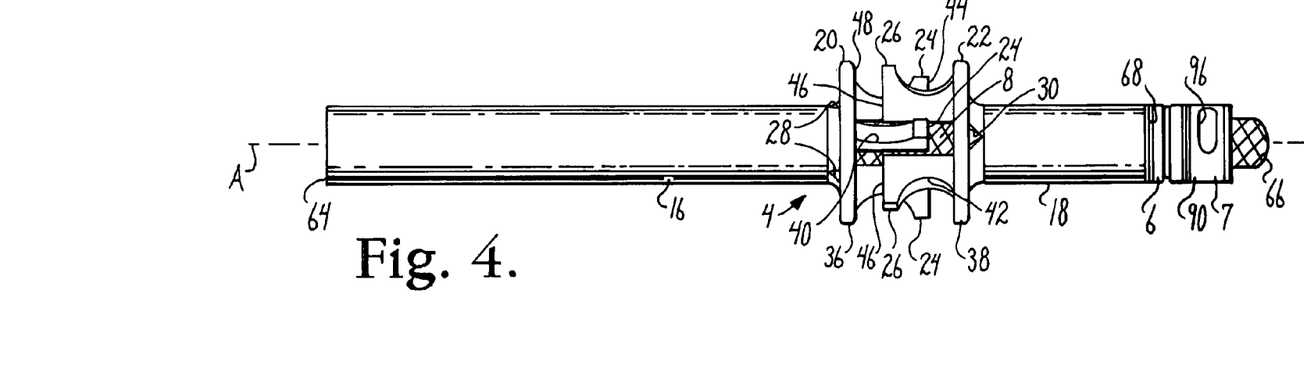
FIG. 4 is an enlarged front elevational view of the assembly of FIG. 1, shown assembled.
Figure 5:
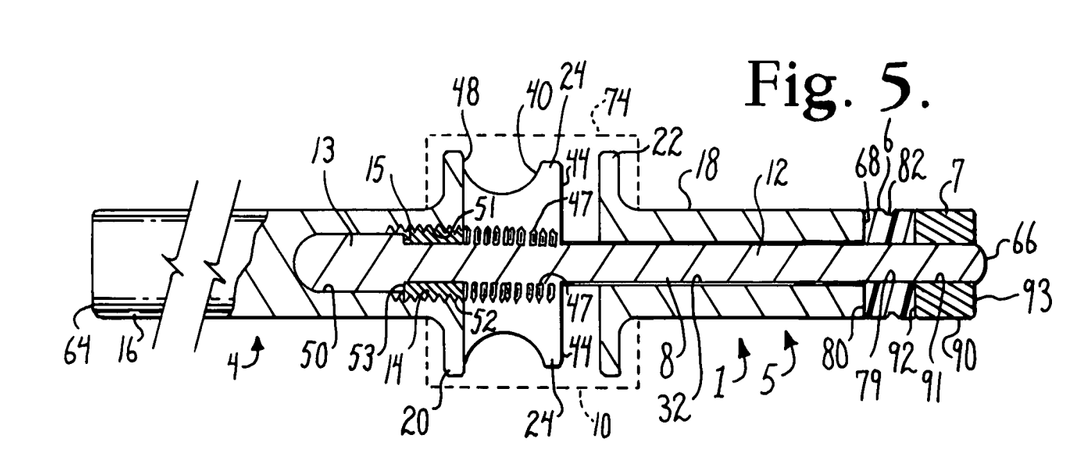
FIG. 5 is an enlarged front elevational view, similar to FIG. 4, with portions broken away to show the detail thereof and the molded spacer shown in phantom.
Figure 6:
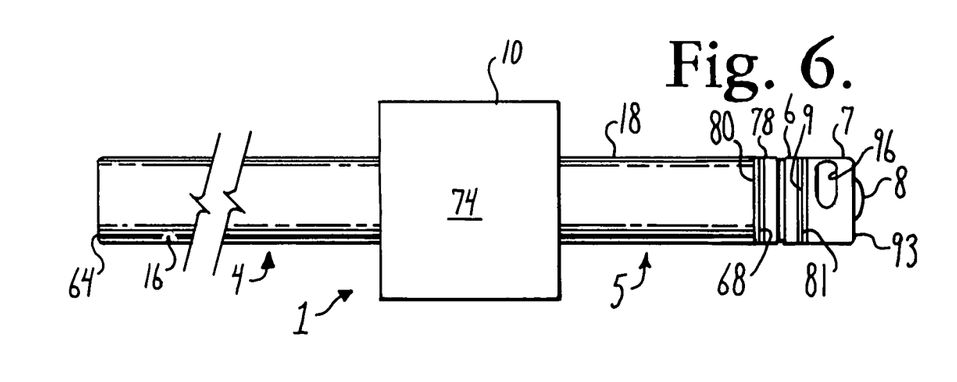
FIG. 6 is an enlarged front elevational view of the assembly of FIG. 1, shown assembled and with the molded spacer.

With particular reference to FIGS. 1-5 the elongate segments 4 and 5 further include respective bone attachment end portions 16 and 18, respective end plates 20 and 22 having respective integral hooked fin or wing members 24 and 26. In the illustrated embodiment, there are three equally spaced fins 24 and 26 extending generally along the axis A from the respective plates 20 and 22. However, in other embodiments according to the invention there may be more than three or less than three hooked fins 24 and 26. Each plate 20 and 22 also includes three apertures or through bores 28 and 30, respectively, spaced substantially equally between the respective fins 24 and 26. The through bores 28 and 30 extend substantially parallel to the axis A. The central core cable 8 is fixed to the plate 20 and extends along the central axis A and between both sets of fins 24 and 26. As best shown in FIGS. 3, 4 and 5, the core 8 also extends through an axial through bore 32 of the segment 5.

As best shown in FIGS. 1-4, each of the hooked or cupped fins 24, as well as the hooked or cupped fins 26, extend axially away from the respective plate 20, 22 (along the axis A) and also extend radially from near the cable 8 to or substantially near a respective outer peripheral substantially cylindrical surface 36 and 38 of the respective plates 20 and 22. Near the peripheral surfaces 36 and 38, the respective fins 24 and 26 include a curved concave or C-shaped hooked or cupped surface 40 and 42, respectively, such surface facing outwardly away from the axis A and running from the respective plates 20 and 22 to near respective end surfaces 44 and 46. Each of the three fins 24 further include threaded inwardly facing surfaces 47 that extend from the plate 20 to the respective end surfaces 44 and are sized and shaped to threadably mate with the threaded annular tap 14, as will be described in detail below. When the segments 4 and 5 are assembled and set in place by the molded spacer 10, the surfaces 44 are near and in substantially uniform spaced relation with the plate 22 and the surfaces 46 are near and in substantially uniform spaced relation with the plate 20. The hooked surfaces 40 and 42 provide structure for mechanical cooperation and grabbing attachment with the molded spacer 10 as will be discussed in greater detail below. Also, as will be described in greater detail below, the spacer 10 is molded about the hooked fins 24 and 26, about the core 8 located between the plates 20 and 22, and through the apertures or bores 28 and 30 of the respective plates 20 and 22 in a manner so as to result in a mechanically connected structure, the elastomeric material completely surrounding the plates 20 and 22 as well as the fins 24 and 26. Thus, during use, bending, twisting or extending movements do not result in a separation or pulling away of the elastomeric material from the surfaces of the plates 20 and 22. In certain embodiments, the elastomeric material of the molded spacer 10 may also adhere to fin, core and plate surfaces and not completely surround the plates 20 and 22. An adhesive may also be added to provide such adherence between the spacer 10 and the plates and fins. Alternatively, in certain embodiments a coating or sleeve may be placed around the core cable 8 portion located between the plates 20 and 22 prior to molding so that the core cable 8 is spaced from the spacer 10 and thus slidably movable with respect to the spacer 10.

The plate 20 includes a surface 48 from which the fins 24 extend. As best illustrated in FIG. 5, formed in the plate surface 48, at and about the axis A, is a central aperture 50, sized and shaped for receiving the plug 13 and a portion of the body 12 of the inner core cable 8. An inner cylindrical threaded section 51 disposed adjacent to the plate surface 48 partially defines the aperture 50. The threaded section 51 is sized to threadably mate with the threaded annular tap 14 at an outer threaded surface 52 thereof. The threaded annular tap 14 further includes an abutment surface 53 and an opposite or top surface having a drive feature 54 thereon. After insertion of the core plug 13 and the threaded annular tap 14 into the aperture 50, the surfaces forming the aperture 50 may also be crimped about the core cable 8. In some embodiments of the invention, the molded spacer 10 will also adhere to the flexible cable 8, fixing the cable 8 to the spacer 10 that is in turn fixed about the plates 20 and 22 and the fins 24 and 26 of the assembly 1.

Figure 7:
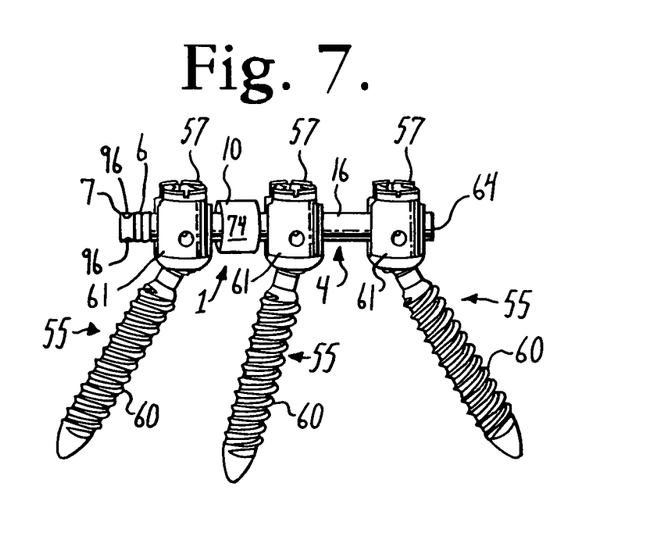
FIG. 7 is a reduced front elevational view of the assembly of FIG. 6 shown with three bone screws.
Figure 8:
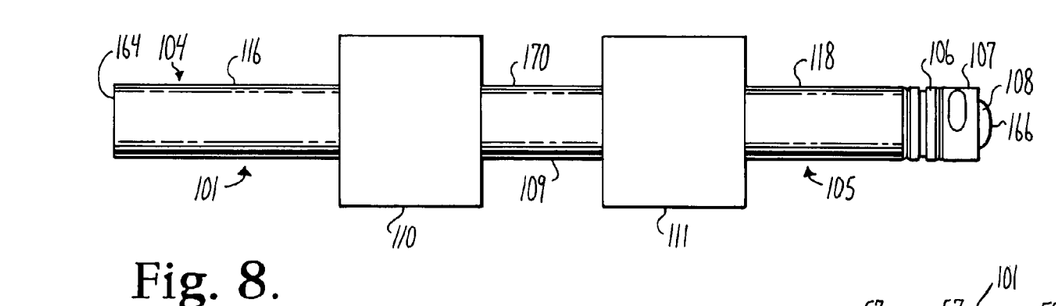
FIG. 8 is an enlarged front elevational view of an alternative embodiment of a dynamic fixation connecting member assembly according to the invention including first and second finned elongate members, an elongate cable core fixed to the first member, an elastic bumper, a crimping ring, a finned sleeve or tube trolley and two outer molded spacers.

The dynamic connecting member assembly 1 cooperates with at least a pair of bone anchors (three shown in FIG. 7), such as the polyaxial bone screws, generally 55 and cooperating closure structures 57 shown in FIG. 7, the assembly 1 being captured and fixed in place at the end portions 16 and 18 by cooperation between the bone screws 55 and the closure structures 57 with the spacer 10 being disposed between an adjacent pair of the bone screws 55.

Because the illustrated end portions 16 and 18 are substantially rigid and cylindrical, the connecting member assembly 1 may be used with a wide variety of bone anchors already available for cooperation with rigid rods including fixed, monoaxial bone screws, hinged bone screws, polyaxial bone screws, and bone hooks and the like, with or without one or more compression inserts, that may in turn cooperate with a variety of closure structures having threads, flanges, or other structure for fixing the closure structure to the bone anchor, and may include other features, for example, break-off tops and inner set screws as well as associated pressure inserts. It is foreseen that the portions 16 and 18 may in other embodiments of the invention have larger and smaller diameters and other cross-sectional shapes, including, but not limited to oval, square, rectangular and other curved or polygonal shapes and be configured in a non-linear relationship. The bone anchors, closure structures and the connecting member assembly 1 are then operably incorporated in an overall spinal implant system for correcting degenerative conditions, deformities, injuries, or defects to the spinal column of a patient.

The illustrated polyaxial bone screws 55 each include a shank 60 for insertion into a vertebra (not shown), the shank 60 being pivotally attached to an open receiver or head 61. The shank 60 includes a threaded outer surface and may further include a central cannula or through-bore disposed along an axis of rotation of the shank to provide a passage through the shank interior for a length of wire or pin inserted into the vertebra prior to the insertion of the shank 60, the wire or pin providing a guide for insertion of the shank 60 into the vertebra. The receiver 61 has a pair of spaced and generally parallel arms that form an open generally U-shaped channel therebetween that is open at distal ends of the arms. The arms each include radially inward or interior surfaces that have a discontinuous guide and advancement structure mateable with cooperating structure on the closure structure 57. The guide and advancement structure may take a variety of forms including a partial helically wound flangeform, a buttress thread, a square thread, a reverse angle thread or other thread like or non-thread like helically wound advancement structure for operably guiding under rotation and advancing the closure structure 57 downward between the receiver 61 arms and having such a nature as to resist splaying of the arms when the closure 57 is advanced into the U-shaped channel. For example, a flange form on the illustrated closure 57 and cooperating structure on the arms of the receiver 61 is disclosed in Applicant's U.S. Pat. No. 6,726,689, which is incorporated herein by reference.

The shank 60 and the receiver 61 may be attached in a variety of ways. For example, a spline capture connection as described in U.S. Pat. No. 6,716,214, and incorporated by reference herein, is used for the embodiment disclosed herein. Polyaxial bone screws with other types of capture connections may also be used according to the invention, including but not limited to, threaded connections, frictional connections utilizing frusto-conical or polyhedral capture structures, integral top or downloadable shanks, and the like. Also, as indicated above, polyaxial and other bone screws for use with connecting members of the invention may have bone screw shanks that attach directly to the segments 16 and 18 may include compression members or inserts that cooperate with the bone screw shank, receiver and closure structure to secure the connecting member assembly to the bone screw and/or fix the bone screw shank at a desired angle with respect to the bone screw receiver that holds the longitudinal connecting member assembly. Furthermore, although the closure structure 57 of the present invention is illustrated with the polyaxial bone screw 55 having an open receiver or head 61, it foreseen that a variety of closure structure may be used in conjunction with any type of medical implant having an open or closed head, including monoaxial bone screws, hinged bone screws, hooks and the like used in spinal surgery.

To provide a biologically active interface with the bone, the threaded shank 60 may be coated, perforated, made porous or otherwise treated. The treatment may include, but is not limited to a plasma spray coating or other type of coating of a metal or, for example, a calcium phosphate; or a roughening, perforation or indentation in the shank surface, such as by sputtering, sand blasting or acid etching, that allows for bony ingrowth or ongrowth. Certain metal coatings act as a scaffold for bone ingrowth. Bio-ceramic calcium phosphate coatings include, but are not limited to: alpha-tri-calcium phosphate and beta-tri-calcium phosphate $(Ca_3(PO_4)_2$, tetra-calcium phosphate $(Ca_4P_2O_9)$, amorphous calcium phosphate and hydroxyapatite $(Ca_{10}(PO_4)_6(OH)_2)$. Coating with hydroxyapatite, for example, is desirable as hydroxyapatite is chemically similar to bone with respect to mineral content and has been identified as being bioactive and thus not only supportive of bone ingrowth, but actively taking part in bone bonding.

The closure structure 57 can be any of a variety of different types of closure structures for use in conjunction with the present invention with suitable mating structure on the interior surface of the upstanding arms the receiver 61. The illustrated closure structure 57 is rotatable between the spaced receiver arms, but could be a twist-in or a slide-in closure structure. The closure 57 includes an outer helically wound guide and advancement structure in the form of a flange form that operably joins with the guide and advancement structure disposed on the interior of the arms of the receiver 61. The illustrated closure structure 57 includes a lower or bottom surface that is substantially planar and may include a point and/or a rim protruding therefrom for engaging the portion 16 or 18 outer cylindrical surface. The closure structure 57 has a top surface with an internal drive feature, that may be, for example, a star-shaped drive aperture sold under the trademark TORX. A driving tool (not shown) sized and shaped for engagement with the internal drive feature is used for both rotatable engagement and, if needed, disengagement of the closure 57 from the arms of the receiver 61. The tool engagement structure may take a variety of forms and may include, but is not limited to, a hex shape or other features or apertures, such as slotted, tri-wing, spanner, two or more apertures of various shapes, and the like. It is also foreseen that the closure structure 57 may alternatively include a break-off head designed to allow such a head to break from a base of the closure at a preselected torque, for example, 70 to 140 inch pounds. Such a closure structure would also include a base having an internal drive to be used for closure removal.

The longitudinal connecting member assembly 1 illustrated in FIGS. 1-7 is elongate, with the attachment portion 16, the plate 20 and the fins 24 being integral and the attachment portion 18, the plate 22 and the fins 26 being integral. The inner core cable 8 is fixed to the plate 20 and is slidingly received in the portion 18. The segments 4 and 5 are preferably made from metal, metal alloys, such as cobalt chrome, or other suitable materials, including but not limited to stainless steel, titanium and nickel titanium (NiTi, a shape memory alloy also commonly referred to by its trade name, Nitinol). The segments 4 and 5 may also be made from plastic polymers such as polyetheretherketone (PEEK), ultra-high-molecular weight-polyethylene (UHMWP), polyurethanes and composites. The core cable 8 with integral or attached plug 13 may also be made from the metals, metal alloys and plastic polymers described herein with respect to the segments 4 and 5, as well as more flexible materials, such as elastomeric strands or cords made from polyethylene or polyurethane blends integral with or otherwise fixed (such as crimped) to a more rigid, solid plug 13 of the same or different material. The elastomeric molded spacer 10 may be made of a variety of materials including plastics and composites. The illustrated spacer 10 is a molded thermoplastic elastomer, for example, polyurethane or a polyurethane blend. However, any suitable polymer material may be used for the spacer 10 and the cable 8.

Specifically, in the illustrated embodiment, the end portion 16 is a substantially solid, smooth uniform cylinder or rod, having a uniform circular cross-section. The end portion 18 is tubular with inner and outer circular cross-sections, and also having an outer profile that is a smooth uniform cylinder having an outer diameter the same as the outer diameter of the portion 16; however, the diameters could be different. The core cable 8 terminates at an end 66 and the tubular end portion 18 terminates at an end 68. The portions 16 and 18 are each sized and shaped to be received in the channel formed between arms of a bone screw receiver 61 with the plates 20 and 22 and the molded spacer 10 disposed between cooperating adjacent bone screws 55. Prior to final assembly, the core cable 8 is typically of a length greater than that shown in the drawing figures so that the core 8 may be grasped by a tool (not shown) near the end 66 and pulled along the axis A in a direction away from the attachment portion 16 in order to place tension on the core cable 8.

The spacer 10 advantageously cooperates with the plates 20 and 22, the fins 24 and 26 and the core cable 8 to provide a flexible or dynamic segment that allows for angular (bending and torsion) and linear displacements (compression and distraction) of the assembly 1. The spacer 10 further provides a smooth substantially cylindrical surface that protects a patient's body tissue from damage that might otherwise occur with, for example, a spring-like dynamic member or a corded member wherein an outer spacer may be pulled away from a cooperating plate or bone screw surface. Thus, the overmolded spacer 10 prevents soft tissues, including scar tissue, from getting between the end plates 20 and 22 and the polymer of the molded spacer 10.

The molded spacer 10 is fabricated about the plates 20 and 22 and the fins 24 and 26, as will be described more fully below, and in the presence of the core cable 8, with molded plastic flowing about the plates, cable and fins. The formed elastomer is substantially cylindrical in outer form with an external substantially cylindrical surface 74 that has the same or substantially similar diameter as the diameter of the outer cylindrical surfaces 36 and 38 of the respective stop or abutment plates 20 and 22. It is foreseen that in some embodiments, the spacer may be molded to be of square, rectangular or other outer and inner cross-sections including curved or polygonal shapes. The portion 16, portion 18 and even the inner cable 8 may also be of other cross-sectional shapes and sizes, including, but not limited to, square, rectangular and other outer and inner cross-sections, including curved or polygonal shapes. The spacer 10 may further include one or more compression grooves (not shown) formed in the surface 74. During the molding process a sleeve or other material (not shown) may be placed about the core cable 8 so that the spacer 10 has in internal surface of a slightly greater diameter than an outer diameter of the cable 8, allowing for axially directed sliding movement of the spacer 10 with respect to the core cable 8.

With reference to FIGS. 1, 4, 5 and 6, the bumper 6 is substantially cylindrical, including an outer surface 78 and an inner surface 79 forming a substantially cylindrical through bore that opens at planar opposed end surfaces 80 and 81 and operatively extends along the axis A. The bumper 6 further includes a compression groove 82 and can be variable in length. The bumper 6 is sized and shaped to slidingly receive the core cable 8 through the inner surface 79. The bumper 6 is preferably made from an elastomeric material such as polyurethane, that may be equal to the stiffness of the spacer or softer. The bumper 6 operatively provides axial tension on the core cable 8, as will be described in greater detail below.

Also with particular reference to FIGS. 1, 4, 5 and 6, the crimping ring 7 is substantially cylindrical and includes an outer surface 90 and an inner surface 91 forming a substantially cylindrical through bore that opens at opposed planar end surfaces 92 and 93 and operatively extends along the axis A. The crimping ring 7 is sized and shaped to receive the elongate core cable 8 through the inner surface 91. The crimping ring 7 further includes a pair of crimp or compression grooves 96 that are pressable and deformable inwardly toward the axis A upon final tensioning of the core 8 and the spacer 10 during assembly of the assembly 1. The crimping ring 7 is preferably made from a stiff, but deformable material, including metals and metal alloys. The ring 7 may also use a set screw to lock it to the cable as opposed to crimping, etc.

In use, at least two bone screws 55 are implanted into vertebrae for use with the longitudinal connecting member assembly 1. Each vertebra may be pre-drilled to minimize stressing the bone. Furthermore, when a cannulated bone screw shank is utilized, each vertebra will have a guide wire or pin (not shown) inserted therein that is shaped for the bone screw cannula of the bone screw shank 60 and provides a guide for the placement and angle of the shank 60 with respect to the cooperating vertebra. A further tap hole may be made and the shank 60 is then driven into the vertebra by rotation of a driving tool (not shown) that engages a driving feature at or near a top of the shank 60. It is foreseen that the screws 55 and the longitudinal connecting member 1 can be inserted in a percutaneous or minimally invasive surgical manner.

The longitudinal connecting member assembly 1 may be assembled to provide a pre-tensioned core cable 8 and pre-compressed spacer 10 and bumper 6 prior to implanting the assembly 1 in a patient. This is accomplished by first providing the segment 4 that has the core cable 8 fixed thereto. With particular reference to FIGS. 2 and 5, to attach the cable 8 to the segment 4, the end 66 of the cable 8 is inserted into the threaded annular tap 14 at the abutment surface 53 and out the surface having the drive 54. The cable 8 is threaded through the threaded annular tap 14 until the surface 15 of the plug 13 contacts the abutment surface 53. The threaded annular tap 14 is then rotated and driven into the threaded portion 51 defining the aperture 50 utilizing a tool (not shown) engaged with the drive feature 54 until the threaded annular tap 14 is fully disposed within the aperture 50. The cable body 12 may initially be longer in the axial direction A than the cable 8 illustrated in the drawing figures to allow for gripping, tensioning and any other manipulation thereof near the end 66. The cable 8 is threaded through the segment 5 with the fins 26 of the plate 22 facing the fins 24 of the segment 4. The core cable 8 is received in the bore 32 and the segment 5 is moved along the core cable 8 toward the plate 20. The fins 24 and 26 are manipulated to be evenly spaced from one another with a desired uniform substantially equal space between the fin ends 46 and the plate 20 and the fin ends 44 and the plate 22. This is performed in a factory setting with the end portions 16 and 18 held in a jig or other holding mechanism that frictionally engages and holds the sections 16 and 18, for example, and the spacer 10 is molded about the plates 20 and 22 as well as the fins 24 and 26 as shown in phantom in FIG. 5. The elastomer of the spacer 10 flows through the plate through bores 28 and 30 as well as around and about each of the fins 24 and 26, the resulting molded spacer 10 surrounding all of the surfaces of the plates 20 and 22 as well as all of the surfaces of the fins 24 and 26. If desired, prior to molding, a sheath or coating may be placed about the core cable 8 so that the spacer 10 material does not contact the core cable 8. However, in other embodiments of the invention, the elastomer is allowed to flow about and contact the core cable 8, that may be pre-tensioned, tensioned after the molding process, or held in a neutral or slackened condition. The jig or holding mechanism may the be released from the portions 16 and 18 after the molding of the spacer 10 is completed. The portions 16 and 18 may be held in a straight or angled position.

Either before or after molding, the bumper 6 is loaded onto the core cable 8 by inserting the cable 8 end 66 into the bore defined by the inner surface 79 with the face 80 facing the toward the surface 68 of the portion 18. The bumper 6 is moved along the core cable 8 until the surface 80 contacts the surface 68. The crimping ring 7 is thereafter loaded onto the cable 8 by inserting the cable 8 end 66 into the bore defined by the inner surface 91 with the face 92 facing the toward surface 81 of the bumper 6. The crimping ring 7 is moved along the core cable 8 until the surface 92 contacts the surface 81. It is noted that due to the symmetrical nature of the bumper 6 and the crimping ring 7, these components may be loaded onto the core cable 8 from either side thereof.

After the crimping ring 7 is loaded onto the core cable 8, manipulation tools (not shown) may be used to grasp the core cable 8 near the end 66 and at the bone anchor attachment portion 16, placing tension on the core cable 8. Furthermore, the spacer 10 and/or the bumper 6 may be compressed, followed by deforming the crimping ring at the crimp grooves 96 and against the core cable 8. When the manipulation tools are released, the crimping ring 7, now firmly and fixedly attached to the core cable 8 holds the spacer 10 and/or the bumper 6 in compression and the spacer and/or the bumper places axial tension forces on the core cable 8, resulting in a dynamic relationship between the core cable 8 and the spacer 10 and/or the bumper 6. Alternatively, the crimping ring 7 may be crimped into frictional engagement with the cable 8 while the cable 8 is in a neutral or slack condition. Then, after implantation, body movements may place the cable 8 in tension and the spacer 10 and/or bumper 6 into compression. In certain embodiments according to the invention, the bumper 6 may be omitted.

With reference to FIG. 7, the assembly 1 is eventually positioned in an open or percutaneous manner in cooperation with the at least two bone screws 55 and shown with three bone screws 55 with the spacer 10 disposed between two adjacent bone screws 55 and the end portions 16 and 18 each within the U-shaped channels of the three bone screws 55. A closure structure 57 is then inserted into and advanced between the arms of each of the bone screws 55. The closure structure 57 is rotated, using a tool (not shown) engaged with the inner drive until a selected pressure is reached at which point the portion 16 or 18 is urged toward, but not completely seated in the U-shaped channels of the bone screws 55. For example, about 80 to about 120 inch pounds pressure may be required for fixing the bone screw shank 60 with respect to the receiver 61 at a desired angle of articulation.

The assembly 1 is thus substantially dynamically loaded and oriented relative to the cooperating vertebra, providing relief (e.g., shock absorption) and protected movement with respect to flexion, extension, distraction, compressive, torsion and shear forces placed on the assembly 1 and the connected bone screws 55. The spacer 10 and cooperating core 8 and fins 24 and 26 allows the assembly 1 to twist or turn, providing some relief for torsional stresses. The spacer 10 in cooperation with the fins 24 and 26, however limits such torsional movement as well as bending movement, compression and distraction, providing spinal support. The core 8 further provides protection against sheer and other stresses placed on the assembly 1.

If removal of the assembly 1 from any of the bone screw assemblies 55 is necessary, or if it is desired to release the assembly 1 at a particular location, disassembly is accomplished by using the driving tool (not shown) with a driving formation cooperating with the closure structure 57 internal drive to rotate and remove the closure structure 57 from the receiver 61. Disassembly is then accomplished in reverse order to the procedure described previously herein for assembly.

Eventually, if the spine requires more rigid support, the connecting member assembly 1 according to the invention may be removed and replaced with another longitudinal connecting member, such as a solid rod, having the same diameter as the end portions 16 and 18, utilizing the same receivers 61 and the same or similar closure structures 57. Alternatively, if less support is eventually required, a less rigid, more flexible assembly, for example, an assembly 1 made without the core 8 or with a spacer 10 made from a more flexible material, or with fewer fins, but with end portions having the same diameter as the portions 16 and 18, may replace the assembly 1, also utilizing the same bone screws 55.

With reference to FIGS. 8-11, the reference numeral 101 generally designates a second embodiment of a non-fusion dynamic stabilization longitudinal connecting member assembly according to the present invention. The connecting member assembly 101 includes first and second elongate segments, generally 104 and 105, an elastic bumper 106, a crimping ring 107, and an inner cable core extension 108, identical or substantially similar to respective segments 4 and 5, elastic bumper 6, crimping ring 7 and inner cable 8 of the assembly 1 previously described herein. The assembly 101 further includes an outer sleeve or tube trolley 109 that is operatively disposed between the segments 104 and 105. As will be described in greater detail below, the sleeve 109 includes fins on either side thereof that cooperate with the fins of the segments 104 and 105, allowing for a longitudinal connector having more than one dynamic portion, each connected by an over-molded spacer. In the embodiment 101, the fins of the segment 104 and one side of the sleeve 109 are surrounded by the over-molded portion 110 and the fins of the segment 105 and the opposite side of the sleeve 109 are surrounded by the over-molded portion 111. The over-molded portions or spacers 110 and 111 are each identical or substantially similar in form and function to the spacer 10 previously described herein with respect to the assembly 1.

The illustrated cable 108 extends along a central longitudinal axis AA of the assembly 101 when the spacers 110 and 111 are molded thereon, connecting the segment 104 with the sleeve 109 and the segment 105 with the sleeve 109, with the cable 108 slidingly received by and extending through the sleeve 109 and the segment 105. The cable 108 may be tensioned prior to molding of the spacers 110 and 111.

Figure 9:
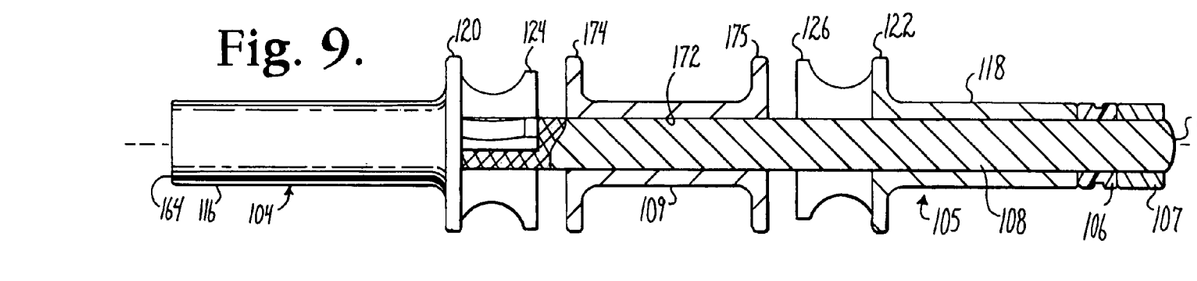
FIG. 9 is an enlarged front elevational view of the assembly of FIG. 8 with portions broken away to show the detail thereof.

With particular reference to FIG. 9, similar to the segments 4 and 5, the elongate segments 104 and 105 further include respective bone attachment end portions 116 and 118, respective end plates 120 and 122 having respective integral hooked fin or wing members 124 and 126. In the illustrated embodiment, there are three equally spaced fins 124 and 126 extending generally along the axis AA from the respective plates 120 and 122. However, in other embodiments according to the invention there may be more than three or less than three hooked fins 124 and 126. The segment 104 further includes an end 164 that is opposite an end 166 of the cable 108. The illustrated central cable 108 is fixed to the section 104 in a manner identical or substantially similar to the threaded attachment of the cable 8 to the section 4 of the assembly 1 as shown in FIG. 5. The cable 108 extends from the plate 120 and along the central axis AA between both sets of fins 124 and 126 and through the sleeve 109.

Figure 10:
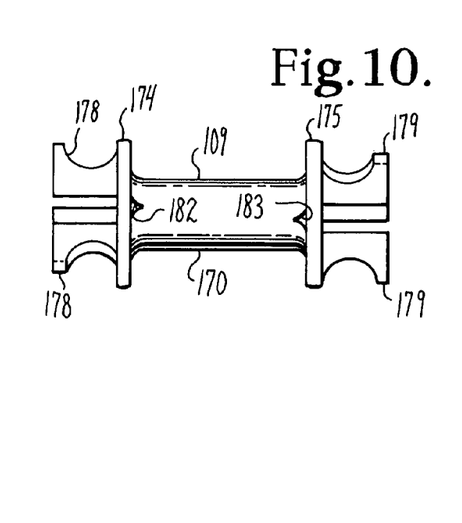
FIG. 10 is an enlarged front elevational view of the sleeve or tube trolley of FIGS. 8 and 9.

With particular reference to FIGS. 9 and 10, the sleeve or tube trolley 109 includes a substantially cylindrical body 170 having an inner lumen or through bore 172 that operatively extends along the axis AA. The sleeve 109 includes a first end plate 174 and an opposite end plate 175. The end plates 174 and 175 have respective integral hooked fin or wing members 178 and 179. In the illustrated embodiment, there are three equally spaced fins 178 and 179 extending generally along the axis AA from the respective plates 174 and 175 that are substantially similar in size and shape with the hooked fins 124 and 126 and the fins 24 and 26 of the assembly 1. However, in other embodiments according to the invention there may be more than three or less than three hooked fins 178 and 179. In operation, the illustrated central cable 108 extends along the central axis AA between both sets of fins 178 and 179 and is slidingly received in the through bore 172. Each plate 174 and 175 also includes three elastomer receiving apertures or through bores 182 and 183, respectively, spaced substantially equally between the respective fins 178 and 179. The through bores 182 and 183 extend substantially parallel to the axis AA.

Figure 11:
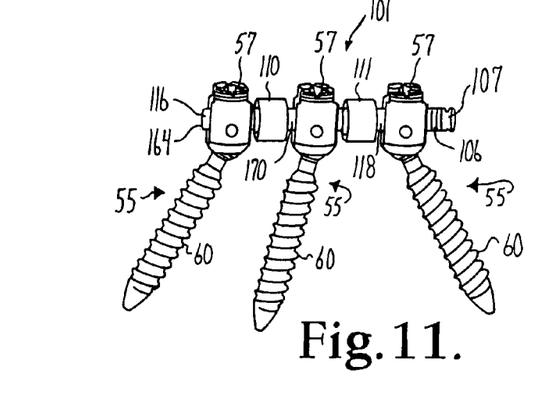
FIG. 11 is a reduced front elevational view of the assembly of FIG. 8 shown with three bone screws.

With reference to FIG. 11, in use, at least three bone screws 55 are implanted into vertebrae for use with the longitudinal connecting member assembly 101 in the same or similar manner as previously discussed herein with respect to the assembly 1. With reference to FIG. 9, the longitudinal connecting member assembly 101 may be assembled to provide a neutral cable 8 and neutral spacers 110 and 111 or a pre-tensioned cable 108 and pre-compressed spacers 110 and 111 and bumper 106 prior to implanting the assembly 101 in a patient. Pre-tensioning is accomplished by first providing the segment 104 with an inner cable that is longer in the axial direction AA than the cable 108 illustrated in the drawing figures so that the cable 108 may be gripped during compression of the spacers 110, 111 or bumper 106 and crimping of the ring 107 onto the cable 108. In all installations, the assembly 101 is assembled by threading the sleeve 109 onto the cable 108, followed by threading the segment 105 onto the cable 108 with the fins 124 of the segment 104 facing the fins 178 of the sleeve 109 and the fins 126 of the segment 105 facing the fins 179 of the sleeve 109. The cable 108 is slidingly received in the bores of the sleeve 109 and the segment 105. The facing fins are manipulated to be evenly spaced from one another with a desired uniform space between the fin ends and facing plates. This is performed in a factory setting with the end portions 116 and 118 and sleeve body 170 held in a jig or other holding mechanism that frictionally engages and holds the sections 116 and 118 and the sleeve 109, for example, and the spacer 110 is molded about the plates 120 and 174 as well as the fins 124 and 178 and the spacer 111 is molded about the plates 122 and 175 as well as the fins 126 and 179. The elastomer of the spacers 110 and 111 flows through the bores formed in the plates as well as around and about each of the fins 124, 126, 178 and 179, the resulting molded spacers 110 and 111 surrounding all of the fins surfaces and at least partially and up to fully surrounding the surfaces of the plates 120, 122, 174 and 175. If desired, prior to molding, a sheath or coating may be placed about the cable 108 so that the elastomeric material of the spacers 110 and 111 does not contact the cable 108. However, in other embodiments of the invention, the elastomer is allowed to flow about and contact the cable 108, that may be tensioned before and/or after the molding process. The jig or holding mechanism may then be released from the portions 116 and 118 and the sleeve body 170 after the molding of the spacers 110 and 111 is completed. The portions 116 and 118 and the body 170 of the sleeve 109 may be held in straight (axial along AA) or angled positions with respect to one another.

Either before or after molding, the bumper 106 is loaded onto the cable 108 and moved along the cable 108 until the bumper 106 contacts the end portion 118. The crimping ring 107 is thereafter loaded onto the core 108 until the ring 107 abuts against the bumper 106. Manipulation tools (not shown) are then used to grasp the cable 108 near the end 166 and at the bone anchor attachment portion 116, placing tension on the cable 108, if desired. Furthermore, the spacers 110 and 111 and/or the bumper 106 may be compressed, followed by deforming the crimping ring at the crimp grooves thereof against the cable 108 as previously described herein with respect to the crimp ring 7 and cable 8 of the assembly 1.

With reference to FIG. 11, the assembly 101 is eventually positioned in an open or percutaneous manner in cooperation with three bone screws 55 with the spacer 110 disposed between two adjacent bone screws 55 and the spacer 111 disposed between two adjacent bone screws 55 with the end portions 116 and 118, and the sleeve body 170 each within the U-shaped channels of one of the three bone screws 55. A closure structure 57 is then inserted into and advanced between the arms of each of the bone screws 55. The closure structure 57 is rotated, using a tool (not shown) engaged with the inner drive until a selected pressure is reached at which point the portion 16 or 18 is urged toward, but not completely seated in the U-shaped channels of the bone screws 55. For example, about 80 to about 120 inch pounds pressure may be required for fixing the bone screw shank 60 with respect to the receiver 61 at a desired angle of articulation.

The assembly 101 is thus substantially dynamically loaded and oriented relative to the cooperating vertebra, providing relief (e.g., shock absorption) and protected movement with respect to flexion, extension, distraction, compressive, torsion and shear forces placed on the assembly 101 and the connected bone screws 55. The spacers 110 and 111 and cooperating cable 108 and fins (124 and 178; and 126 and 179) allow the assembly 101 to twist or turn, providing some relief for torsional stresses. The spacers 110 and 111 and cooperating over-molded fins, however limit such torsional movement as well as bending movement, compression and distraction, providing spinal support. The cable 108 further provides protection against sheer stresses placed on the assembly 101.

If removal of the assembly 101 from any of the bone screw assemblies 55 is necessary, or if it is desired to release the assembly 101 at a particular location, disassembly is accomplished by using the driving tool (not shown) with a driving formation cooperating with the closure structure 57 internal drive to rotate and remove the closure structure 57 from the receiver 61. Disassembly is then accomplished in reverse order to the procedure described previously herein for assembly.

It is to be understood that while certain forms of the present invention have been illustrated and described herein, it is not to be limited to the specific forms or arrangement of parts described and shown.

What is claimed and desired to be secured by Letters Patent is as follows:

1. In a medical implant assembly having at least two bone attachment structures cooperating with a longitudinal connecting member, the improvement wherein the longitudinal connecting member comprises:
   a) first and second rigid segments, each rigid segment having a cylindrical end plate with an enlarged radius and an integral fin extending axially therefrom, the fins being in circumferentially spaced and overlapping relationship, the second rigid segment having a through bore extending axially therethrough;
   b) a single inner core with a first end fixed to the first rigid segment and extending entirely through the through bore of the second rigid segment, the inner core overlapping each of the fins, the inner core being at least somewhat elastic; and
   c) a molded elastomeric spacer substantially surrounding each end plate, the fins and a portion of the inner core.

2. The improvement of claim 1 wherein the fin of each segment is a first fin and including a second fin on each segment.

3. The improvement of claim 1 further comprising an elastic bumper receiving the inner core through a bumper through bore near a second end of the inner core.

4. The improvement of claim 3 wherein at least one of the elastic bumper and the molded elastomeric spacer is held in a compressed state by a structure fixed to the inner core second end.

5. The improvement of claim 4 wherein the structure fixed to the inner core second end is a crimping ring.

6. The improvement of claim 1 wherein the inner core is pre-tensioned.

7. The improvement of claim 1 further comprising a rigid sleeve disposed between the first and second rigid segments, the sleeve having a lumen extending axially therethrough, the inner core slidingly received entirely through the lumen, the molded elastomeric spacer including first and second portions, the first portion attaching the first rigid segment to the sleeve and the second portion attaching the second rigid segment to the sleeve.

8. The improvement of claim 7 wherein the sleeve has at least one integral fin extending axially therefrom.

9. The improvement of claim 7 wherein the sleeve has at least two integral fins extending from opposite ends of the sleeve.

10. In a medical implant assembly having at least two bone attachment structures cooperating with a longitudinal connecting member, the improvement wherein the longitudinal connecting member comprises:
   a) first and second rigid elongate segments, the segments aligned along a central axis, each segment having a cylindrical end-plate with at least one integral fin extending axially therefrom and radially from the axis, the fins being in circumferentially spaced, overlapping relation along the axis;
   b) a single inner cable fixed to the end of the first segment and extending between the fins and entirely through the second segment along the central axis, the inner cable being at least somewhat elastic; and
   c) a molded elastomeric spacer substantially surrounding each end-plate, each fin and a portion of the inner cable overlapping the fins.

11. The improvement of claim 10 wherein the at least one fin is a plurality of fins.

12. The improvement of claim 10 wherein the at least one fin is at least a pair of fins on each elongate segment, the fins of the first segment disposed between the fins of the second segment.

13. The improvement of claim 12 wherein the fins are in substantially equal spaced relation to one another.

14. The improvement of claim 10 wherein the at least one fin has a concave surface.

15. The improvement of claim 14 wherein the concave surface faces outwardly away from the axis.

16. The improvement of claim 10 wherein the molded elastomeric spacer surrounds each end plate.

17. In a medical implant assembly having at least three bone anchors cooperating with a longitudinal connecting member, the improvement wherein the longitudinal connecting member comprises:
  a) a rigid first elongate member having a first longitudinal axis, the first elongate member being sized and shaped for attachment to at least one bone anchor, the elongate member having a first end plate and a first curvate fin fixed to the end plate, the curvate fin extending along the first axis and radially outward from the first axis;
  b) a rigid second elongate member having a second longitudinal axis, the second elongate member being sized and shaped for attachment to at least one bone anchor, the second elongate member having a first axial through bore, a second end plate and a second curvate fin fixed to the second end plate, the second curvate fin extending along the second axis and radially outward from the second axis; the first and second fins being circumferentially spaced from each other;
  c) a rigid sleeve sized and shaped for attachment to at least one bone anchor, the sleeve disposed between the first and second elongate members, the sleeve having a second axial through bore, third and fourth end plates, a third curvate fin extending from the third plate and a fourth curvate fin extending from the fourth plate;
  d) a first molded elastomeric spacer surrounding the first and third end plates and holding the first and third fins in substantially spaced relation with one another;
  e) a second molded elastomeric spacer surrounding the second and fourth end plates and holding the second and fourth fins in substantially spaced relation to one another; and
  f) a single elastic inner cable with a first end fixed to the first elongate member adjacent to the first end plate and slidingly received through the first and second through bores.

18. The improvement of claim 17 further comprising
  a) an elastic bumper slidingly received on the inner cable near a second end thereof; and
  b) a crimping structure abutting the bumper and fixed to the inner cable second end.

19. The improvement of claim 17 wherein the first fin is a plurality of fins and the third fin is a plurality of fins, each first fin being at least partially disposed between a pair of third fins.

20. The improvement of claim 17 where in the second fin is a plurality of fins and the fourth fin is a plurality of fins, each second fin being at least partially disposed between a pair of fourth fins.

21. A medical implant assembly having at least two bone attachment structures cooperating with a longitudinal connecting member, wherein the longitudinal connecting member comprises:
  a) an anchor member portion having a first rigid segment in locked engagement with one of at least two bone attachment structures, the first rigid segment including a radially extending end plate, the anchor member portion having a single tensionable elastic inner core extension of reduced diameter, the core extension having first and second ends and extending from the first rigid segment end plate along a substantially central axis of the longitudinal connecting member, the core extension first end being fixed to an aperture in the end plate;
  b) a second rigid segment having a through bore extending entirely therethrough, the core extension being received within the through bore, in slidable relationship therewith and extending completely therethrough, the second rigid segment being in a locked engagement with the other of the at least two bone attachment structures;
  c) at least one compressible outer member having the core extension extending entirely therethrough, the outer member being positioned between the at least two bone attachment structures, surrounding the end plate and being in compressive engagement with the second rigid segment, the outer member being made of a moldable material;
  d) at least one elastic bumper positioned around the core extension and in slidable relation therewith, the bumper having non-overlapping compressive engagement with the second rigid segment, the bumper being positioned opposite the outer member; and
  e) an end ring compressed against the bumper with a non-overlapping engagement and secured to a second end of the core extension, whereby the inner core extension is at least partially tensioned; wherein
  f) when in use, the core extension is in tension due to the elastic compression of the compressible outer member and the bumper, thereby providing a dynamic stabilization connecting member for the at least two bone attachment structures; and wherein
  g) the anchor member first rigid segment and the second rigid segment have spaced apart and opposed axial extending structure with overlapping compressive engagement on opposite ends of the at least one compressible outer member for torsion and shear control of the second rigid segment with respect to the anchor member.

22. The assembly according to claim 21, wherein
  a) the compressible outer member overlaps the first rigid segment.

23. The assembly according to claim 21, wherein
  a) the compressible outer member overlaps the second rigid segment.

24. A medical implant assembly having at least two bone attachment structures cooperating with a longitudinal connecting member, wherein the longitudinal connecting member comprises:
  a) a first rigid bone attachment portion with first and second ends, the second end having an aperture extending axially therein toward the first end;
  b) a second rigid bone attachment portion with third and fourth ends and a through bore extending axially entirely therethrough so as to join the third and fourth ends; the second and third ends each include at least one curvate fin extending axially therefrom, the fins being spaced and overlapping with each other;
  c) an inner core having a body with fifth and sixth ends, the fifth end being received within the aperture and fixed therein, the body extending through the second bone attachment portion through bore such that the sixth end is disposed outside of the fourth end; and d) a compressible molded outer sleeve covering the second and third ends and at least a portion of the body; wherein e) the inner core is tensioned such that the outer sleeve is compressed at the second and third ends.

25. The longitudinal connecting member according to claim 24, further comprising:
a) a plug end attached to the inner core fifth end; wherein
b) the fifth end is fixed within the aperture by a press fit.

26. The longitudinal connecting member according to claim 24, further comprising:
a) a threaded annular tap; wherein
b) the aperture includes a thread sized and shaped to cooperate with the threaded annular tap so as to fix the fifth end within the aperture.

27. The longitudinal connecting member according to claim 24, wherein:
a) the inner core is a cord.

28. The longitudinal connecting member according to claim 24, wherein:
a) the inner core is at least partially elastic.

29. The longitudinal connecting member according to claim 24, wherein:
a) the connecting member includes a longitudinal axis and the inner core extends along the axis between the fins.

30. A medical implant assembly having at least two bone attachment structures cooperating with a longitudinal connecting member, wherein the longitudinal connecting member comprises:
a) a first elongate bone attachment portion with a first integral end plate at one end, the end plate having an aperture extending axially therein, the first portion being attached to at least one bone attachment structure;
b) a second elongate bone attachment portion with a second integral end plate and a through bore extending axially entirely therethrough, the second portion being attached to a second bone attachment structure;
c) a core member having a core end received within the aperture of the first portion and fixed therein, the core member extending entirely through the through bore of the second bone attachment portion bore;
d) an extension extending axially from each endplate;
e) a compressible outer sleeve overlapping the extensions from the end plates;
f) an end ring received on and fixed to the core member;
g) a bumper received on the core member between the second bone attachment portion and the end ring; and
h) the core member being tensioned such that the outer sleeve is compressed against the end plates and the bumper is compressed between the end ring and the second bone attachment portion.

31. A medical implant assembly having at least two bone attachment structures cooperating with a longitudinal connecting member, wherein the longitudinal connecting member comprises:
a) a first rigid bone attachment portion with first and second ends, the second end having an aperture extending axially therein toward the first end and a structure extending longitudinally outward therefrom;
b) a second rigid bone attachment portion with third and fourth ends and a through bore extending axially entirely therethrough so as to join the third and fourth ends;
c) an inner core having a body with fifth and sixth ends, the fifth end being received within the aperture and fixed therein and overlapped by the longitudinally extending structure, the body extending through the second bone attachment portion through bore such that the sixth end is disposed outside of the fourth end; and
d) a compressible outer sleeve covering the longitudinally extending structure and at least a portion of the body; the second and third ends each include at least one extending structure therefrom, each structure being spaced apart and overlapped by the outer sleeve; wherein
e) the inner core is tensioned such that the outer sleeve is compressed at the second and third ends.

32. The longitudinal connecting member according to claim 31, wherein:
a) the connecting member includes a longitudinal axis and the inner core is flexible.

* * * * *